United States Patent
Gunn, III

(10) Patent No.: US 10,365,224 B2
(45) Date of Patent: Jul. 30, 2019

(54) LABEL-FREE OPTICAL SENSORS

(75) Inventor: Lawrence Cary Gunn, III, Encinitas, CA (US)

(73) Assignee: GENALYTE, INC., San Diego, CA (US)

( * ) Notice: Subject to any disclaimer, the term of this patent is extended or adjusted under 35 U.S.C. 154(b) by 0 days.

(21) Appl. No.: 12/746,747

(22) PCT Filed: Dec. 8, 2008

(86) PCT No.: PCT/US2008/085988
§ 371 (c)(1),
(2), (4) Date: Nov. 8, 2010

(87) PCT Pub. No.: WO2009/076323
PCT Pub. Date: Jun. 18, 2009

(65) Prior Publication Data
US 2011/0045472 A1 Feb. 24, 2011

Related U.S. Application Data

(60) Provisional application No. 61/005,372, filed on Dec. 6, 2007.

(51) Int. Cl.
*G01N 21/84* (2006.01)
*G01N 21/77* (2006.01)
(Continued)

(52) U.S. Cl.
CPC ......... *G01N 21/7746* (2013.01); *G01N 21/84* (2013.01); *G01N 33/54373* (2013.01); *G01N 33/574* (2013.01); *C12Q 1/6869* (2013.01)

(58) Field of Classification Search
CPC .... C12Q 1/6869; G01N 1/7746; G01N 21/84; G01N 33/54373
See application file for complete search history.

(56) References Cited

U.S. PATENT DOCUMENTS 4,078,052 A 3/1978 Papahadjopoulos
4,224,179 A 9/1980 Schneider
(Continued)

FOREIGN PATENT DOCUMENTS

CA 2 355 816 6/2000
CA 2 555 962 9/2007
(Continued)

OTHER PUBLICATIONS

Song et al "Detection of oligonucleotide hybridizaiton at femtomolar level and sequence-specific gene anaylsis of the *Arabidopsis thaliana* leaf extract with an unitrasensitive surface plasmon resonance spectrometer" Nucleic Acids Research, 2002, 30(14): e72, pates 1-11.*

(Continued)

*Primary Examiner* — Betty J Forman
(74) *Attorney, Agent, or Firm* — Knobbe, Martens, Olson & Bear, LLP

(57) ABSTRACT

Techniques, apparatus and systems are described for performing label-free monitoring of processes. In one aspect, a label-free monitoring system includes an array of label-free optical sensors to detect an optical signal in response to synthesis of one or more target genetic structures. Each label-free optical sensor is functionalized with a respective target genetic structure. The system also includes a fluid flow control module that includes fluid receiving units to provide paths for different fluids to flow into the fluid flow control module and at least one switch connected to the fluid receiving units to selectively switch among the fluid receiving units to receive a select sequence of the fluids through the fluid receiving units. The select sequence of the fluids includes at least a dNTP or base. A fluid channel is connected between the fluid flow control module and the array of sensors to allow the select sequence of the fluids to flow (Continued)

| 101 | Lower Cladding |
| 106 | Substrate |
| 202 | Waveguide |
| 203 | Ring | from the fluid flow control module to the array of label-free optical sensors.

18 Claims, 9 Drawing Sheets

(51) Int. Cl.
*G01N 33/543* (2006.01)
*G01N 33/574* (2006.01)
*C12Q 1/6869* (2018.01)

(56) References Cited

U.S. PATENT DOCUMENTS

| | | | |
|---|---|---|---|
| 4,235,871 A | 11/1980 | Papahadjopoulos et al. | |
| 4,308,166 A | 12/1981 | Marchetti et al. | |
| 4,310,506 A | 1/1982 | Baldeschwieler et al. | |
| 4,394,372 A | 7/1983 | Taylor | |
| 4,474,893 A | 10/1984 | Reading | |
| 4,485,054 A | 11/1984 | Mezei et al. | |
| 4,508,703 A | 4/1985 | Redziniak et al. | |
| 4,522,803 A | 6/1985 | Lenk et al. | |
| 4,714,681 A | 12/1987 | Reading | |
| 4,925,648 A | 5/1990 | Hansen et al. | |
| 5,192,549 A | 3/1993 | Barenolz et al. | |
| 5,270,163 A | 12/1993 | Gold et al. | |
| 5,475,096 A | 12/1995 | Gold et al. | |
| 5,478,755 A | 12/1995 | Attridge et al. | |
| 5,539,082 A | 7/1996 | Nielsen et al. | |
| 5,567,588 A | 10/1996 | Gold et al. | |
| 5,573,920 A | 11/1996 | Randle | |
| 5,595,877 A | 1/1997 | Gold et al. | |
| 5,601,819 A | 2/1997 | Wong et al. | |
| 5,637,459 A | 6/1997 | Burke et al. | |
| 5,681,702 A | 10/1997 | Collins et al. | |
| 5,683,867 A | 11/1997 | Biesecker et al. | |
| 5,705,337 A | 1/1998 | Gold et al. | |
| 5,714,331 A | 2/1998 | Buchardt et al. | |
| 5,719,262 A | 2/1998 | Buchardt et al. | |
| 5,939,021 A | 8/1999 | Hansen et al. | |
| 6,043,060 A | 3/2000 | Imanishi | |
| 6,210,891 B1* | 4/2001 | Nyren et al. | 435/6.12 |
| 6,268,490 B1 | 7/2001 | Imanishi et al. | |
| 6,583,399 B1 | 6/2003 | Hunziker et al. | |
| 6,670,461 B1 | 12/2003 | Wengel et al. | |
| 6,958,241 B2 | 10/2005 | Martin et al. | |
| 7,083,920 B2 | 8/2006 | Werner et al. | |
| 7,108,863 B2 | 9/2006 | Zalipsky et al. | |
| 7,183,759 B1 | 2/2007 | Malendevish et al. | |
| 7,208,174 B2 | 4/2007 | Huwyler et al. | |
| 7,391,936 B2* | 6/2008 | Pau | B01L 3/502715 385/12 |
| 7,528,403 B1* | 5/2009 | Borselli | G02B 6/12004 257/101 |
| 7,778,499 B2 | 8/2010 | Janz et al. | |
| 7,796,262 B1 | 9/2010 | Wang et al. | |
| 9,846,126 B2 | 12/2017 | Gunn, III et al. | |
| 9,921,165 B2 | 3/2018 | Bailey et al. | |
| 9,983,206 B2 | 5/2018 | Bailey et al. | |
| 2002/0012930 A1 | 1/2002 | Rothberg et al. | |
| 2002/0037526 A1 | 3/2002 | Tashiro et al. | |
| 2003/0017579 A1* | 1/2003 | Corn et al. | 435/287.2 |
| 2003/0027327 A1* | 2/2003 | Cunningham et al. | 435/287.2 |
| 2003/0027328 A1 | 2/2003 | Cunningham et al. | |
| 2003/0039978 A1 | 2/2003 | Hannah | |
| 2003/0096302 A1 | 5/2003 | Yguerabide et al. | |
| 2003/0153023 A1 | 8/2003 | Starzl et al. | |
| 2004/0023396 A1 | 2/2004 | Boyd et al. | |
| 2004/0145752 A1 | 7/2004 | Angeley | |
| 2004/0180362 A1 | 9/2004 | Lazar et al. | |
| 2004/0191765 A1 | 9/2004 | Mozdy et al. | |
| 2005/0014179 A1* | 1/2005 | Karlsson et al. | 435/6 |
| 2005/0250094 A1 | 11/2005 | Storhoff et al. | |
| 2006/0087656 A1 | 4/2006 | Barford et al. | |
| 2006/0119859 A1 | 6/2006 | Su et al. | |
| 2006/0182659 A1 | 8/2006 | Unlu et al. | |
| 2006/0194232 A1* | 8/2006 | Turner et al. | 435/6 |
| 2006/0215165 A1 | 9/2006 | Melman | |
| 2006/0256350 A1 | 11/2006 | Nolte et al. | |
| 2007/0081163 A1 | 4/2007 | Liang et al. | |
| 2007/0147732 A1 | 6/2007 | Sanders | |
| 2007/0195321 A1 | 8/2007 | Soussaine et al. | |
| 2007/0237460 A1* | 10/2007 | Fan et al. | 385/39 |
| 2008/0026394 A1 | 1/2008 | Labgold et al. | |
| 2008/0038738 A1 | 2/2008 | Weigum et al. | |
| 2008/0129997 A1* | 6/2008 | Yi | G02B 6/12007 356/337 |
| 2008/0131939 A1* | 6/2008 | Roper | 435/91.2 |
| 2008/0138801 A1* | 6/2008 | He | 435/6 |
| 2008/0160622 A1 | 7/2008 | Su et al. | |
| 2008/0181710 A1 | 7/2008 | Nakazawa et al. | |
| 2008/0204760 A1 | 8/2008 | Gollier et al. | |
| 2009/0170212 A1 | 7/2009 | Van Dijk et al. | |
| 2009/0309049 A1 | 12/2009 | Van Dijk et al. | |
| 2010/0009456 A1 | 1/2010 | Prins et al. | |
| 2010/0105566 A1 | 4/2010 | Bieniarz et al. | |
| 2010/0124787 A1 | 5/2010 | Nitkowski et al. | |
| 2010/0165351 A1 | 7/2010 | Xu et al. | |
| 2011/0275061 A1 | 11/2011 | Weidemaier et al. | |
| 2012/0092650 A1 | 4/2012 | Gunn, III et al. | |
| 2013/0157283 A1 | 6/2013 | Yung et al. | |
| 2013/0261010 A1 | 10/2013 | Bailey et al. | |
| 2013/0295688 A1 | 11/2013 | Bailey et al. | |
| 2014/0070082 A1 | 3/2014 | Guo et al. | |
| 2014/0273029 A1 | 9/2014 | Bailey et al. | |
| 2017/0176433 A1 | 6/2017 | Hauenstein et al. | |
| 2018/0202937 A1 | 7/2018 | Gunn, III et al. | |
| 2018/0299438 A1 | 10/2018 | Bailey et al. | |

FOREIGN PATENT DOCUMENTS

| | | |
|---|---|---|
| EP | 0 740 156 | 10/1996 |
| EP | 2347247 | 7/2011 |
| EP | 2635710 | 9/2013 |
| EP | 2825885 | 1/2015 |
| JP | 01-287427 | 11/1989 |
| JP | 2924707 | 7/1999 |
| JP | 2002-526773 | 8/2002 |
| JP | 2004-354068 | 12/2004 |
| JP | 2004-361087 | 12/2004 |
| JP | 2005-140683 | 6/2005 |
| JP | 2005-321244 | 11/2005 |
| JP | 2006-029883 | 2/2006 |
| JP | 2006-153643 | 6/2006 |
| JP | 2006-234810 | 9/2006 |
| JP | 2006-267052 | 10/2006 |
| JP | 2007-220864 | 8/2007 |
| JP | 2007-309886 | 11/2007 |
| JP | 2008-057997 | 3/2008 |
| JP | 2010-511864 | 4/2010 |
| JP | 2010-518394 | 5/2010 |
| JP | 2012-507035 | 3/2012 |
| JP | 5656853 | 12/2014 |
| WO | WO 91/000360 | 1/1991 |
| WO | WO 92/000509 | 1/1992 |
| WO | WO 92/005793 | 4/1992 |
| WO | WO 92/008802 | 5/1992 |
| WO | WO 93/017715 | 9/1993 |
| WO | WO 98/039352 | 9/1998 |
| WO | WO 99/014226 | 3/1999 |
| WO | WO 00/020861 | 4/2000 |
| WO | WO 00/056746 | 9/2000 |
| WO | WO 00/056748 | 9/2000 |
| WO | WO 00/066604 | 11/2000 |
| WO | WO 01/000641 | 1/2001 |
| WO | WO 01/001455 | 1/2001 |
| WO | WO 01/007455 | 2/2001 |
| WO | WO 03/052097 | 6/2003 |
| WO | WO 2005/066612 A2 | 7/2005 |
| WO | WO 2005/080602 | 9/2005 |
| WO | WO 2007/081163 | 7/2007 |
| WO | WO 2008/054170 | 5/2008 |
| WO | 2008/070437 | 6/2008 |
| WO | WO 2008/081719 | 7/2008 |

(56) References Cited

FOREIGN PATENT DOCUMENTS

| WO | WO 2008/097199 | 8/2008 |
|---|---|---|
| WO | 2009/076323 | 6/2009 |
| WO | WO 2009/069009 A1 | 6/2009 |
| WO | WO 2009/075473 A1 | 6/2009 |
| WO | WO 2010/062627 A2 | 6/2010 |
| WO | WO 2011/091037 A2 | 7/2011 |
| WO | WO 2012/061778 A2 | 5/2012 |
| WO | WO 2013/138251 A1 | 9/2013 |
| WO | WO 2014/143637 A | 9/2014 |

OTHER PUBLICATIONS

Ramachandran, et al., 'A Universal Biosensing Platform Based on Optical Micro-Ring Resonators,' Biosensors and Bioelectronics, Sep. 21, 2007, vol. 23, pp. 939-944, see abstract pp. 940-942.
McKendry, et al., 'Multiple Label-Free Biodetection and Quantitative DNA-Binding Assays on a Nanomechanical Cantilever Array,' PNAS, Jul. 23, 2002, vol. 99, No. 15, ppp. 9783-9788, see pp. 978309785.
Vollmer, et al., Multiplexed DNA Quatification by Spectroscopic Shift of Two Microsphere Cavities, Biophysical Journal, Sep. 2003, vol. 85, pp. 1974-1979, see pp. 1974-1977.
Li, et al., Sequence-Specific Label Free DNA Sensors Based on Silicon Nanowires, Nano Lett., Aug. 1, 2004, vol. 4., No. 2, pp. 245-247, see pp. 246-247.
European Search Report dated Mar. 31, 2014 of corresponding European Patent Application No. 11838918.8—10 pages.
Office Action dated Mar. 10, 2015 in corresponding European Application No. 11838918.8, 4 pgs.
Office Action dated Oct. 13, 2015 in corresponding European Application No. 11838918.8, 4 pgs.
International Search Report dated Jun. 16, 2010 for International Patent Application No. PCT/US2009/062268.
International Search Report and Written Opinion dated May 24, 2013 in corresponding PCT Application No. PCT/US2013/030274.
International Preliminary Report on Patentability and Written Opinion dated May 3, 2011 for International Patent Application No. PCT/US2009/062268.
International Search Report and Written Opinion dated Jun. 16, 2014 in Application No. PCT/US2014/026852, filed Mar. 13, 2014.
International Search Report and Written Opinion dated Jun. 1, 2012 in Application Mo. PCT/US2011/59454, 22pgs.
Office Action dated Jan. 14, 2014 in corresponding Japanese Application No. 2011-534688, 20 pgs.
Decision to Grant dated Sep. 24, 2014 in corresponding Japanese Application No. 2011-534688, 3 pgs.
Office Action dated Oct. 20, 2015 in corresponding Japanese Application No. 2014-238245, 3 pgs.
International Written Opinion dated May 26, 2009 in Application No. PCT/US2008/085988, 4 pgs.
Bailey er al. A Robust Silicon Phtotonic Platform for Multiparameter Biological Analysis. Proc. Of SPIE. 2009, vol. 7220, p. 72200N-6. (Table of Conents for Proc. Of SPIE. 2009, vol. 7220 uploaded to establish priority and avialable from <http://spie.org/x648.html?product_id=799296&origin_id=x4325&start_volume_number=7200&end_volume_number=7299&start_at=21>) esp: abstract, p. 72200N-4 first paragraph; p. 72200N-2 top of page; p. 72200N-3 first paragraph; Figs, 5, 6, 7.
Kajiura M et al: "Biosensing by optical waveguide spectroscopy based on localized surface plasmon resonance of gold nanoparticles used as a probe or as a label", Journal of Colloid and Interface Science, Academic Press, New York, NY, US, vol. 335, No. 1,Jul. 1, 2009 (Jul. 1, 2009), pp. 140-145.
Matthew S. Luchansky et al: "Silicon Photonic Microring Resonators for Quantitative Cytokine Detection and T-Cell Secretion Analysis", Analytical Chemistry, vol. 82, No. 5,Mar. 1, 2010 (Mar. 1, 2010), pp. 1975-1981.
Matthew S. Luchansky et al: "Sensitive on-chip detection of a protein biomarker in human serum and plasma over an extended dynamic range using silicon photonic microring resonators and sub-micron beads", Lab on a Chip, vol. 11, No. 12, Jan. 1, 2011 (Jan. 1, 2011), p. 2042.
Abraham J. Qavi et al: "Anti-DNA:RNA Antibodies and Silicon Photonic Microring Resonators: Increased Sensitivity for Multiplexed micro RNA Detection", Analytical Chemistry, vol. 83, No. 15, Aug. 1, 2011 (Aug. 1, 2011), pp. 5949-5956.
Allen et al., "Nuclear factor-kappaB-related serum factors as longitudinal biomarkers of response and survival in advanced oropharyngeal carcinoma," Clin. Cancer Res. 13(11): 3182-3190, (2007).
Anderson et al., "The human plasma proteome: history, character, and diagnostic prospects," Mol. Cell. Proteomics, 1: 845-867, (2002).
Angelopoulos et al., "Cytokines in Alzheimer's disease and vascular dementia," Int. J. Neurosci., 118(12): 1659-1672, (2008).
Anoop et al., "CSF Biomarkers for Alzheimer's Disease Diagnosis," Int. J. Alzheimers Dis., 2010: 1-12, (2010).
Azevedo et al., "Stability of free and immobilised peroxidase in aqueous-organic solvents mixtures," J. Mol. Catal. B: Enzym., 15: 147-153, (Nov. 2001).
Baker et al., "Plasma and cerebrospinal fluid interleukin-6 concentrations in posttraumatic stress disorder," Neuroimmunomodulation, 9(4): 209-217, (2001).
Bell et al., "Interleukin-6 and interleukin-10 in cerebrospinal fluid after severe traumatic brain injury in children," J. Neurotrauma, 14: 451-457, (1997).
Blennow et al., "Cerebrospinal fluid and plasma biomarkers in Alzheimer disease," Nat Rev Neurol, 6(3): 131-144, (2010).
Blum-Degen et al., "Interleukin-1 beta and interleukin-6 are elevated in the cerebrospinal fluid of Alzheimer's and de novo Parkinson's disease patients," Neurosci. Lett., 202(1-2): 17-20, (1995).
Boguslawski et al., "Characterization of monoclonal antibody to DNA.RNA and its application to immunodetection of hybrids," J. Immunological Methods, 89(1): 123-130, (1986).
Braasch et al., "Novel antisense and peptide nucleic acid strategies for controlling gene expression," Biochemistry, 41(14): 4503-4510, (2002).
Byeon et al., "Efficient bioconjugation of protein capture agents to biosensor surfaces using aniline-catalyzed hydrazone ligation," Langmuir, 26(19): 15430-15435, (2010).
Byeon et al., "Multiplexed evaluation of capture agent binding kinetics using arrays of silicon photonic microring resonators," Analyst, 136(17): 3430-3433, (2011).
Capule et al., "An ELISA-based method to quantify the association of small molecules with aggregated amyloid peptides," Anal. Chem., 84(3): 1786-1791, (2012).
Casebolt et al., "Monoclonal Antibody Solution Hybridization Assay for Detection of Mouse Hepatitis Virus Infection," Journal of Clinical Microbiology, 30(3): 608-612, (1992).
Chen et al., "Plasmon-Enhanced Colorimetric ELISA with Single Molecule Sensitivity," Nano Lett., 11(4): 1826-1830, (2011).
Clark et al., "Characteristics of the microplate method of enzyme-linked immunosorbent assay for the detection of plant viruses," J. Gen. Virol., 34: 475-483, (1977).
Conyers et al., "Chromogenic substrates for horseradish peroxidase," Anal. Biochem., 192: 207-211, (1991).
Ellison et al., "Standard additions: myth and reality," Analyst, 133: 992-997, (2008).
Engelborghs et al., "Unchanged levels of interleukins, neopterin, interferon-gamma and tumor necrosis factor-alpha in cerebrospinal fluid of patients with dementia of the Alzheimer type," Neurochem. Int., 34: 523-530, (1999).
"EnzMet TM HRP Detection Kit for IHC / ISH", Nanoprobes Inc., Yaphank, NY, Jan. 2008. http://www.nanoprobes.com/products/EnzMet-SISH-enzyme-metallography-for-ISH-and-IHC.html, downloaded Jan. 19, 2017.
Fagan et al., "Cerebrospinal fluid biomarkers of Alzheimer's disease," Biomarkers Med., 4(1): 51-63, (2010).
Fliss et al., "Anti-DNA.RNA antibodies: an efficient tool for non-isotopic detection of Listeria species through a liquid-phase hybridization assay," Appl Microbiol Biotechnol, 43(4): 717-724, (1995).

(56) References Cited

OTHER PUBLICATIONS

Fortin et al., "Imaging of DNA hybridization on microscopic polypyrrole patterns using scanning electrochemical microscopy (SECM): the HRP bio-catalyzed oxidation of 4-chloro-1-naphthol," Analyst, 131: 186-193, (2006).
Gabay, "Interleukin-6 and chronic inflammation," Arthritis Res. Ther., 8(Suppl 2): S3, 6 pp., (2006).
Gauldie et al., "Interferon beta 2/B-cell stimulatory factor type 2 shares identity with monocyte-derived hepatocyte-stimulating factor and regulates the major acute phase protein response in liver cells," Proc. Natl. Acad. Sci. U.S.A., 84(20): 7251-7255, (1987).
Gorris et al., "Mechanistic Aspects of Horseradish Peroxidase Elucidated through Single-Molecule Studies," Am. Chem. Soc., 131(17): 6277-6282, (2009).
Hansson et al., "Association between CSF biomarkers and incipient Alzheimer's disease in patients with mild cognitive impairment: a follow-up study," Lancet Neurol, 5(3): 228-234, (2006).
Heath et al., "Nanotechnology and Cancer," Annu. Rev. Med., 59: 251-265, (2008).
Hosoda et al., "A comparison of chromogenic substrates for horseradish peroxidase as a label in steroid enzyme immunoassay," Chem. Pharm. Bull. (Tokyo), 34: 4177-4182, (1986).
Huell et al., "Interleukin-6 is present in early stages of plaque formation and is restricted to the brains of Alzheimer's disease patients," Acta Neuropathol., 89(6): 544-551, (1995).
Ihenetu et al., Pharmacological characterisation of cannabinoid receptors inhibiting interleukin 2 release from human peripheral blood mononuclear cells, European Journal of Pharmacology 454 (2003) 207-215.
Iqbal et al., "Label-Free Biosensor Arrays Based on Silicon Ring Resonators and High-Speed Optical Scanning Instrumentation," IEEE J. Sel. Top. Quantum Electron., 16(3): 654-661, (2010).
Ivanov et al., "Chip-Based Nanostructured Sensors Enable Accurate Identification and Classification of Circulating Tumor Cells in Prostate Cancer Patient Blood Samples," Anal. Chem., 85(1): 398-403, (2013).
Jia et al., "Cerebrospinal fluid tau, Aβ1-42 and inflammatory cytokines in patients with Alzheimer's disease and vascular dementia," Neurosci. Lett., 282: 12-16, (2005).
Khuseyinova et al., "Determination of C-reactive protein: comparison of three high-sensitivity immunoassays," Clin. Chem., 49: 1691-1695, (2003).
Kindt et al., "Chaperone probes and bead-based enhancement to improve the direct detection of mRNA using silicon photonic sensor arrays," Anal. Chem., 84(18): 8067-8074, (2012).
Kindt J.T. et al., "Subpicogram Per Milliliter Detection of Interleukins Using Silicon Photonic Microring Resonators and an Enzymatic Signal Enhancement Strategy," Anal Chem 85: 10653-10657 (2013).
Konry et al., "Microsphere-based rolling circle amplification microarray for the detection of DNA and proteins in a single assay," Anal. Chem., 81(14): 5777-5782, (2009).
Kostelny et al., "Formation of a bispecific antibody by the use of leucine zippers," J. Immunol., 148(5): 1547-1553, (1992).
Krishnan et al., "Attomolar detection of a cancer biomarker protein in serum by surface plasmon resonance using superparamagnetic particle labels," Agnew Chem. Int. Ed. Engl., 50: 1175-1178, (Feb. 2011).
Lafer et al., "The effect of anti-Z-DNA antibodies on the B-DNA-Z-DNA equilibrium," J Biol Chem, 261(14): 6438-6443, (1986).
Li et al., "Detection of protein biomarkers using RNA aptamer microarrays and enzymatically amplified surface plasmon resonance imaging," Anal. Chem., 79(3): 1082-1088, (2007).
Llano et al., "Cerebrospinal fluid cytokine dynamics differ between Alzheimer disease patients and elderly controls," Alzheimer Dis. Assoc. Disord., 26(4): 322-328, (2012).
Luchansky et al., "Rapid, multiparameter profiling of cellular secretion using silicon photonic microring resonator arrays," J. Am. Chem. Soc., 133(50): 20500-20506, (2011).
Supplemental Materials for Luchansky, M.S., et al. "Sensitive on-chip detection of a protein biomarker in human serum and plasma over an extended dynamic range using silicon photonic microring resonators and sub-micron beads," The Royal Society of Chemistry (Supp): 1-14 (2011).
Martinez et al., "Increased cerebrospinal fluid fas (Apo-1) levels in Alzheimer's disease. Relationship with IL-6 concentrations," Brain Res., 869(1-2): 216-219, (2000).
Marz et al., "Interleukin-6 (IL-6) and soluble forms of IL-6 receptors are not altered in cerebrospinal fluid of Alzheimer's disease patients," Neurosci. Lett., 239(1): 29-32, (1997).
Munge et al., "Nanostructured immunosensor for attomolar detection of cancer biomarker interlukin-8 using massively labeled supermagnetic particles," Agnew Chem. Int. Ed. Engl., 50(34): 7915-7918, (Aug. 2011).
Nielsen et al., "Sequence-selective recognition of DNA by strand displacement with a thymine-substituted polyamide," Science, 254(5037): 1497-1500, (1991).
Olson et al., "Growth factors and cytokines/chemokines as surrogate biomarkers in cerebrospinal fluid and blood for diagnosing Alzheimer's disease and mild cognitive impairment," Exp. Gerontol., 45(1): 41-46, (2010).
Palandra et al., "Highly specific and sendsitive measurements of human and monkey interleukin 21 using sequential protein and tryptic peptide immunoaffinity LC-MS/MS," Anal. Chem., 85(11): 5522-5529, (2013).
Parker et al., Monoclonal Antibodies against the Human Epidermal Growth Factor Receptor from A431 Cells, The Journal of Biological Chemistry, 259(15), 9906-9912, 1984.
Riley et al., "Stability of DNA/anti-DNA complexes. II. Salt lability and avidity," J Immunol, 124(1): 1-7, (1980).
Rissin et al., "Single-molecule enzyme-linked immunosorbent assay detects serum proteins at subfemtomolar concentrations," Nat. Biotechnol., 28: 595-599, (2010).
Sheehan et al., "Detection limits for nanoscale biosensors," J. Nano Lett., 5: 803-807, (2005).
Sokolova et al., "Monocyte Chemoattractant Protein-1 Plays a Dominant Role in the Chronic Inflammation Observed in Alzheimer's Disease," Brain Pathol., 19(3): 392-398, (2009).
Soleymani et al., "Hierarchical Nanotextured Microelectrodes Overcome the Molecular Transport Barrier to Achieve Rapid, Direct Bacterial Detection," ACS Nano, 5(4): 3360-3366, (2011).
Squires et al., "Making it stick: convection, reaction and diffusion in surface-based biosensors," Nat. Biotechnol., 26(4): 417-426, (2008).
Steensberg et al., "Cerebrospinal fluid IL-6, HSP72, and TNF-alpha in exercising humans," Brain Behav. Immun., 20(6): 585-589, (2006).
Stelmasiak et al., "Interleukin-6 concentration in serum and cerebrospinal fluid in multiple sclerosis patients," Med. Sci. Monit., 6(6): CR1104-CR1108, (2000).
Stollar et al., "Immunochemical approaches to gene probe assays," Anal. Biochem., 161(2): 387-394, (1987).
Stollar, "Molecular analysis of anti-DNA antibodies," FASEB J, 8(3): 337-342, (1994).
Tarkowski et al., "Early intrathecal production of interleukin-6 predicts the size of brain lesion in stroke," Stroke, 26: 1393-1398, (1995).
Tarkowski et al., "Intracerebral production of tumor necrosis factor-alpha, a local neuroprotective agent, in Alzheimer disease and vascular dementia," J. Clin. Immunol., 19(4): 223-230, (1999).
Tsai et al., "Cerebrospinal fluid interleukin-6, prostaglandin E2 and autoantibodies in patients with neuropsychiatric systemic lupus erythematosus and central nervous system infections," Scand. J. Rheumatol., 23(2): 57-63, (1994).
Tutt et al., "Trispecific F(ab')3 derivatives that use cooperative signaling via the TCR-CD3 complex and CD2 to activate and redirect resisting cytotoxic T cells," J. Immunol., 147(1): 60-69, (1991).
Vandermeeren et al., "Detection of Proteins in Normal and Alzheimer's Disease Cerebrospinal Fluid with a Sensitive Sandwich Enzyme-Linked Immunosorbent Assay," Journal of Neurochemistry, 61(5): 1828-1834, (1993).
Veitch, "Horseradish peroxidase: a modern view of a classic enzyme," Phytochemistry, 65(3): 249-259, (2004).

(56) References Cited

OTHER PUBLICATIONS

Vollmer et al., "Whispering-gallery-mode biosensing: label-free detection down to single molecules," Nature Methods, 5: 591-596, (2008).
Wang et al., "Cyclohexene Nucleic Acids (CeNA): Serum Stable Oligonucleotides that Activate RNase H and Increase Duplex Stability with Complementary RNA," J. Am. Chem. Soc., 122(36): 8595-8602, (2000).
Washburn et al., "Label-free quantitation of a cancer biomarker in complex media using silicon photonic microring resonators," Anal. Chem. 81(22): 9499-9506, (2009).
eBioscience Enzyme Linked Immunosorbent Assay 2010, ELISA Protocols, http://www.ebioscience.com/media/pdf/best-protocols/enzyme-linked-immunosorbent-assay-elisa.pdf.
SABiosciences Single Analyte Elisa Kits 2010, Product List, http://www.sabiosciences.com/singleelisa.php.
Elia, G; Silacci, M; Scheurer, S; Scheuermann, J; Neri, 0 Affinity-capture reagents for protein arrays. Trends Biotech. 2002, 20, S19-S22.
Phelan, M L; Nock, S Generation of bioreagents for protein chips. Proteomics 2003, 3, 2123-2134.
Brody, EN; Gold, L Aptamers as therapeutic and diagnostic agents. J. Biotechol. 2000, 74,5-13.
Kodadek, T; Reddy, M M; Olivos, H J; Bach hawat-Si kder, K; Alluri, P G Synthetic Molecules as Antibody Replacements. Acc. Chem. Res. 2004,37,711-718.
Engvall, E; Perlmann, P Enzyme-linked immunosorbent assay (ELISA) quantitative assay for immunoglobulin G. Immunochem 1971, 8,871-874.
http://www.luminexcorp.com/.
Kodadek, T Protein microarrays: prospects and problems. Chem. Biot. 2001, 8, 105-115.
Sun, Y S; Landry, J P; Fei, Y Y; Zhu, X 0; Luo, J T; Wang, X B; Lam, K S Effect of Fluorescently Labeling Protein Probes on Kinetics of Protein-Ligand Reactions. Langmuir 2008, 24, 13399-13405.
Qavi, A J; Washburn, A L; Byeon, J-Y; Bailey, R C Label-free technologies for quantitative multiparameter biological analysis. Anal. Bioanal. Chem. 2009, 394, 121-135.
Homola, J; Vee, S S; Gauglitz, G Surface plasmon resonance sensors: review. Sens. Actuators B. 1999, 54,3-15.
Stuart, 0 A; Haes, A J; Yonzon, C R; Hicks, E M; Van Duyne, R P Biological Applications of Localized Surface Plasmon Resonance Phenomena. IEEE Proc.—Nanobiotechnol.2005, 152, 13-32.
Bailey, R C; Parpia, M; Hupp, J T Sensing via Optical Interference. Materials Today 2005, 8, 46-52.
Wolfbeis, 0 S Fiber-Optic Chemical Sensors and Biosensors. Anal. Chem. 2002, 74, 2663-2678.
Boozer, C; Kim, G; Cong, S; Guan, H; Londergan, T Looking towards label-free biomolecular interaction analysis in a high-throughput format: a review of new surface plasmon resonance technologies. Curro Op. Biotech. 2006, 17, 400-405.
Vahala, K J Optical microcavities. Nature 2003, 424, 839-846.
Luchansky, M S; Washburn, A L; Martin, T A; Iqbal, M; Gunn, L C; Bailey, R C Characterization of the evanescent field profile and bound mass sensitivity of a label-free silicon photonic microring resonator biosensing platform. Biosens. Bioelectron.2010, doi:1 0.1016/j.bios.201 0.1 007.1 010.
Washburn, A L; Luchansky, M S; Bowman, A L; Bailey, R C Quantitative Multiplexed Detection of Five Protein Biomarkers Using Arrays of Silicon Photonic Microring Resonators. Anal. Chem. 2010, 82,69-72.
Eddowes, M J Direct immunochemical sensing: basic chemical principles and fundamental limitations. Biosensors 1987, 3, 1-15.
Byeon, J-Y; Bailey, R C Label-Free, Multiplexed Determination of Aptamer and Antibody Capture Agent Binding Affinities Using Silicon Photonic Microring Resonator Arrays and Implications for Sensitive Biomolecule Detection. Chem. Commun., 136, 3430-3433, 2011.
Qavi, A J; Mysz, T M; Bailey, R C Label-Free Detection of DNA and Isothermal Discrimination of Single Nucleotide Polymorphisms via Kinetic Desorption Rates using Silicon Photonic Microring Resonator Arrays. J. Am. Chem. Soc. 6827-6833, 2011.
Qavi, A J; Bailey, R C Multiplexed Detection and Label-Free Quantitation of MicroRNAs Using Arrays of Silicon Photonic Microring Resonators. Angew. Chem. 2010, 49,4608-4611.
Wolter, A; Niessner, R; Seidel, M Preparation and Characterization of Functional Poly(ethylene glycol) Surfaces for the Use of Antibody Microarrays. Anal. Chem. 2007, 79,4529-4537.
Ladd, J; Zhang, Z; Chen, S; Hower, J C; Jiang, S Zwitterionic Polymers Exhibiting High Resistance to Nonspecific Protein Adsorption from Human Serum and Plasma. Biomacromolecules 2008, 9, 1357-1361.
Soderberg, 0; Leuchowius, K-J; Kamali-Moghaddam, M; Jarvius, M; Gustafsdottir, S; Schell meiner, E; Gullberg, M; Jarvius, J; Landegren, U Proximity Ligation: A Specific and Versatile Tool for the Proteomic Era. Genetic Eng. 2007, 28, 85-93.
Gulberg, M; Fredriksson, S; Taussig, M; Jarvius, J; Gustafsdottir, S; Landegren, U A sense of closeness: protein detection by proximity ligation. Curro Op. Biotech. 2003, 14, 82-86.
Heyduk, E; Dummit, B; Chang, Y-H; Heyduk, T Molecular Pincers: Antibody-Based Homogeneous Protein Sensors. Anal. Chem. 2008, 80,5152-5159.
Reddy, M M; Bachhawat-Sikder, K; Kodadek, T Transformation of Low-Affinity Lead Compounds into High-Affinity Protein Capture Agents. Chem. Biol. 2004, 11, 1127-1137.
Agnew, H D; Rohde, R D; Millward, S W; Nag, A; Yeon, W-S; Hein, J; Pitram, S M; A.A., T; Burns, V M; Krom, R J; Fokin, V V; Sharpless, K B; Heath, J R Iterative In Situ Click Chemistry Creates Antibody-like Protein-Capture Agents. Angew. Chem. 2009, 48,4944-4948.
Krasinski, A; Radic, Z; Manetch, R; Raushel, J; Taylor, P; Sharpless, K B; Kolb, H C In Situ Selection of lead Compounds by Click Chemistry: Target-Guided Optimization of Acetylcholinesterase Inhibitors. J. Am. Chem. Soc. 2005, 127, 6686-6692.
Manetsch, R; Krasinski, A; Radic, Z; Raushel, J; Taylor, P; Sharpless, K B; Kolb, H C In Situ Click Chemistry: Enzyme Inhibitors Made to Their Own Specifications. J. Arn. Chern. Soc. 2004, 126, 12809 12818.
Erlanson, D A; Iam, J W; Wiesmann, C; Iuong, T N; Simmons, R I; Delano, W I; Choong, I C; Burdett, M T; Flanagan, W M; Iee, D; Gordon, E M; O'Brien, T In situ assembly of enzyme inhibitors using extended tethering. Nature Biotech. 2003, 21, 308-314.
Bachhawat-Sikder, K; Kodadek, T Mixed-Element Capture Agents: A Simple Strategy for the Construction of Synthetic, High-Affinity Protein Capture Ligands. J. Arn. Chern. Soc. 2003, 125,9550-9551.
Naffin, J I; Han, Y; Olivos, H J; Reddy, M M; Sun, T; Kodadek, T Immobilized Peptides as High-Affinity Capture Agents for Self-Associating Proteins. Chern. Biol. 2003, 10, 251-259.
Niemeyer, C M Semisynthetic DNA-Protein Conjugates for Biosensing and Nanofabrication. Angew. Chem. Inti. Ed. 2010, 49, 1200-1216.
Bailey, R C; Kwong, G A; Radu, C G; Witte, 0 N; Heath, J R DNA-Encoded Antibody Libraries: A Unified Platform for Multiplexed Cell Sorting and Detection of Genes and Proteins. J. Am. Chern. Soc. 2007, 129, 1959-1967.
Ge, Y. Turner, A P F Molecularly Imprinted Sorbent Assays: Recent Developments and Applications. Chern. Eur. J. 2009, 15, 8100-8107.
Scheck, R A; Francis, M B Regioselective Labeling of Antibodies through N-Terminal Transamination. ACS Chern. Biol. 2007, 2, 247-251.
Niemeyer, C M; Adler, M; Wacker, R Detecting antigens by quantitative immuno-PCR. Nature Protocols 2007, 2, 1918-1930.
Bayley, H; Cremer, P S Stochastic sensors inspired by biology. Nature 2001, 413, 226-230.
Thaxton, C S; Rosi, N L; Mirkin, C A Optically and chemically encoded nanoparticie materials for DNA and protein detection. MRS Bulletin 2005, 30, 376-380.
Palik, E, Ed. Handbook of Optical Constants of Solids; Academic Press: San Diego, CA,1998.

(56) References Cited

OTHER PUBLICATIONS

Bailey, R C; Nam, J-M; Mirkin, C A; Hupp, J T Real-Time Multicolor DNA Detection with Chemoresponsive Diffraction Gratings and Nanoparticle Probes. J. Am. Chem. Soc. 2003, 125, 13541-13547.
Hao, E. Li, S. Bailey, R C; Zou, S; Schatz, G C; Hupp, J T The Optical Properties of Metal Nanoshells. J. Phys. Chem. B. 2004, 108, 1224-1229.
Hao, E; Bailey, R C; Hupp, J T; Schatz, G C; Li, S Synthesis and Optical Properties of 'Three-Pointed' Star-Shaped Gold Nanoparticles. Nano. Lett. 2004, 4, 327-330.
Bailey, R C; Hupp, J T Large-Scale Resonance Amplification of Optical Sensing of Volatile Compounds with Chemoresponsive Visible-Region Diffraction Gratings. J. Am. Chem. Soc. 2002, 124, 6767-6774.
Fang, W.; Bucholz, D.B.; Bailey, R.C.; Hupp, J.T.; Chang, R.P.H.; Cao, H. Detection of Chemical Species Using Ultraviolet Microdisk Lasers. Appl. Phys. Lett. 2004, 85, 3666-3668.
Krioukov, E.; Klunder, D.J.W.; Driessen, A; Greve, J.; Otto, C. Sensor based on an integrated optical microcavity. Opt. Lett. 2002, 27, 512-514.
Vollmer, F.; Braun, D.; Libchaber, A; Khoshima, M.; Teraoka, I.; Arnold, S. Protein detection by optical shift of a resonant microcavity. Appl. Phys. Lett. 2002, 80, 4057-4059.
Chao, C.-Y.; Guo, L.J. Biochemical sensors based on polymer microrings with sharp asymmetrical resonances. Appl. Phys. Lett. 2003, 83, 1527-1529.
Schmidt, J. Stochastic sensors. J. Mater. Chem. 2005, 15,831-840.
Bayley, H.; Martin, C.R. Resistive-Pulse Sensing—From Microbes to Molecules. Chem. Rev. 2000, 100, 2575-2594.
Armani, A.M.; Kulkarni, R.P.; Fraser, S.E.; Flagan, R.C.; Vahala, K.J. Label-free single-molecule detection with optical m icrocavities. Science 2007, 317,783-787.
Perez-Luna, V.H.; O'Brien, M.J.; Opperman, K.A.; Hampton, P.O.; Lopez, G.P.; Klumb, L.A.; Stayton, P.S. Molecular Recognition between Genetically Engineered Streptavidin and Surface-Bound Biotin. J. Am. Chem. Soc. 1999, 121,6469-6478.
Berezovski, M.; Nutiu, R.; Li, Y.; Krylov, S.N. Affinity Analysis of a Protein-Aptamer Complex Using Nonequilibrium Capillary Electrophoresis of Equilibrium Mixtures. Ana/. Chem. 2003, 75, 1382-1386.
Wayment, J.R.; Harris, J.M. Controlling Binding Site Densities on Glass Surfaces. Ana/. Chem. 2006, 78,7841-7849.
Pierres, A.; Touchard, D.; Benoliel, A.-M.; Bongrand, P. Dissecting Steptavidin-Biotin Interaction with a Laminar Flow Channel. Biophys. J. 2002, 82, 3214-3223.
Cao, L.; Chen, H.-Z.; Zhu, L.; Zhang, X.-B.; Wang, M. Optical absorption and structural studies of erbium biphthalocyanine sublimed films. Mater. Lett. 2003, 57, 4309-4314.
Su, X.-C.; Huber, T.; Dixon, N.E.; Otting, G. Site-Specific Labelling of Proteins with a Rigid Lanthanide-Binding Tag. ChemBioChem 2006, 7, 1599-1604.
Turner, E.H.; Cohen, D.; Pugsley, H.R.; Gomez, D.G.; Whitmore, C.D.; Zhu, C.; Dovichi, N.J. Chemical cytometry: the chemical analysis of single cells. Anal. Bioanal. Chem. 2008, 390, 223-226.
Ellington, A.D.; Szostak, J.W. In vitro selection of RNA molecules that bind specific ligands. Nature 1990,346,818-822.
Tuerk, C.; Gold, L. Systematic evolution of ligands by exponential enrichment: RNA ligans to bacteriophage T4 DNA polymerase. Science 1990, 249, 505-510.
Supplementary European Search Report dated Jan. 8, 2016 in corresponding European Application No. EP 13760958, 9 pgs.
Luxton R. et al: "Use of External Magnetic Fields to Reduce Reaction Times in an Immunoassay Using Micrometer-Sized Paramagentic Particles as Labels (Magentoimmunoassay)", Analytical Chemistry, Americal Chemical Society, US, vol. 76, No. 6, Mar. 15, 2004 (Mar. 15, 2004), pp. 1715-1719, XP001196657, ISSN: 0003-2700, DOI: 10.1021/AC034906+.
Gijs et al: Microfluidic Application of Magentic Particles for Biological Analysis and Catalysis:, Chemical Review, American Chemical Society, US, vol. 110, No. 3, Jan. 1, 2010 (Jan. 1, 2010), pp. 1518-1563, XP007917138, ISSN: 0009-2665, DOI: 10.1021/CR9001929 [retrieved on Apr. 12, 2009].
Office Action in corresponding Japanese application No. 2014-238245 dated Jul. 26, 2016, 9 pgs.
Schuler et al., "A Disposable and Cost Efficient Microfluidic Device for the Rapid Chip-Based Electrical Detection of DNA", Biosensors and Bioelectronics 25 (2009) 15-21.
European Search Report dated Jul. 25, 2017 in EP Application No. 08858855.3, 14 pgs.
Ho, D., et al., "DNA as a Force Sensor in an Aptamer-Based Biochip for Adenosine." Anal. Chem. 81, 3159-3164 (2009).
Jiang, S. & Cao, Z., "Ultralow-Fouling, Functionalizable, and Hydrolyzable ZwitterionicMaterials and Their Derivatives for Biological Applications." Adv. Mater. 22, 920-932 (2010).
Koch, B., et al., Hurricane: A simplified optical resonator for optical-power-based sensing with nanoparticle taggants. Sens. Actuators, B 147, 573-580 (2010).
Puchner, E.M. & Gaub. H.E., "Force and function: probing proteins with AFM-based force spectroscopy." Curr. Opin. Struct. Biol. 19, 605-614 (2009).
Sano, T., Smith, C. & Cantor, C., "immuno-PCR: very sensitive antigen detection by means of specific antibody-DNA conjugates." Science 258, 120-122 (1992).
Severin, P.M.D., Ho, D. & Gaub., H.E., "A high throughput molecular force assay for protein-DNA interactions." Lab Chip 11, 856-862 (2011).
Stroock, A.D., et al., Chaotic Mixer for Microchannels. Science 295, 647-651 (2002).
Arnold., S., et al., "Whispering gallery mode bio-sensor for label-free detection of single molecules: thermos-optic vs. reactive mechanism", Opt. Express 18, 281-287 (2010).
Berry., S,M., et al., "One-step purification of nucleic acid for gene expression analysis via Immiscible Filtration Assisted by Surface Tension (IFAST)", Lab Chip 11, 1747-1753 (2011).
Chen., J., et al., "Facile Synthesis of Gold-Silver Nanocages with Controllable Pores on the Surface", J. Am. Chem. Soc. 128, 14776-14777 (2006).
Chen, J., et al., "Gold Nanocages: Bioconjugation and Their Potential Use as Optical Imaging Contrast Agents", Nano Lett. 5, 473-477 (2005).
Chen, J., et al., "Immuno God Nanocages with Tailored Optical Properties for Targeted Photothermal Destruction of Cancer Cells", Nano Lett. 7, 1318-1322 (2007).
Choi, J., et al., "Immuno-Hybridization Chain Reaction for Enhancing Detection of Individual Cytokine-Secreting Human Peripheral Mononuclear Cells", Anal. Chem. 83, 6890-6895 (2011).
Dirks, R.M., et al., "Triggered amplification by hybridization chain reaction", Proc.Natl. Acad. Sci. U.S.A. 101, 15275-15278 (2004).
Evanko, D., "Hybridization chain reaction", Nat Meth 1, 186-187 (2004).
Frisk, M., et al., "Synaptotagmin II peptide-bead conjugate for botulinum toxin enrichment and detection in microchannels", Biosens. Bioelectron. 26, 1929-1935 (2011).
Gusev, Y., et al., "Rolling Circle Amplification: An New Approach to Increase Sensitivity for Immunohistochemistry and Flow Cytometry", The American journal of pathology 159, 63-69 (2001).
Haddadpour, A., et al., "Metallic nanoparticle on micro ring resonator for bio optical detection and sensing", Biomed. Opt. Express 1, 378-384 (2010).
Hornola, J., "Surface Plasmon Resonance Sensors for Detection of Chemical arid Biological Species", Chem. Rev. 108, 462-493 (2008).
Ligler F., "A Perspective on Optical Biosensors and Integrated Sensor Systems", Anal. Chem. 81, 519-526 (2008).
Lizardi, P., et al., "Mutation detection and single-molecule counting using isothermal rolling-circle amplification", Nat. Genet. 19, 225-232 (1998).
Luchansky, M., et al., "High-Q Optical Sensors for Chemical and Biological Analysis", Anal. Chem. im press, DOI:10.1021/ac2029024 (2012).

(56) References Cited

OTHER PUBLICATIONS

Moon, G., et al., "A New Theranostic System Based on Gold Nanocages and Phase-Change Materials with Unique Features for Photoacoustic Imaging and Controlled Release", *J. Am. Chem. Soc.* 133, 4762-4765 (2011).
Soelberg, S., et al., "Surface Plasmon Resonance (SPR) Detection Using Antibody-Linked Magnetic Nanoparticles for Analyte Capture, Purification, Concentration and Signal Amplification", *Anal. Chem.* 81, 2357-2363 (2009).
Wang, Y., et al., "Magnetic Nanoparticle-Enhanced Biosensor Based on Grating-Coupled Surface Plasmon Resonance", *Anal. Chem.* 83, 6202-6207 (2011).
Washburn, A., et al., "DNA-encoding of Antibodies Improves Performance and Allows Parallel Evaluation of the Binding Characteristics of Multiple Protein Capture Agents in a Surface-Bound Immunoassay Format", *Anal. Chem.* 83, 3572-3580 (2011).
Washburn, A., et al., "Photonics-on-a-Chip: Recent Advances in Integrated Waveguides as Enabling Detection Elements for Real-World, Lab-on-a-Chip Biosensing Applications", *Analyst* 136, 227-236 (2011).
Williams, M., et al., "A practical guide to the staggered herringbone mixer", *Lab Chip* 8, 1121-1129 (2008).
1994 Pierce Chemical Company Catalog, Technical Section on Cross-Linking, pp. 155-200.
Alvarez-Garcia et al., "MicroRNA Functions in Animal Development and Human Disease", Development, 2005, vol. 132, No. 21, pp. 4653-4662.
Ambros et al., "A Uniform System for MicroRNA Annotation", RNA, 2003, vol. 9, pp. 277-279.
Arima et al., "Surface Plasmon Resonance and Surface Plasmon Field-Enhanced Fluorescence Spectroscopy for Sensitive Detection of Tumor Markers", Biosensors and Biodetection, 2009, pp. 3-20.
Arnold et al., "Shift of Whispering-Gallery Modes in Microspheres by Protein Adsorption", Optics Letters, Feb. 15, 2003, vol. 28, No. 4, pp. 272-274.
Babak et al., "Probing MicroRNAs with Microarrays: Tissue Specificity and Functional Inference", RNA, 2004, vol. 10, pp. 1813-1819.
Bartel et al., "MicroRNAs: At the Root of Plant Development?" Plant Physiology, Jun. 2003, vol. 132, pp. 709-717.
Bartel, David P., "MicroRNAs: Genomics, Biogenesis, Mechanism, and Function", Cell, Jan. 23, 2004, vol. 116, pp. 281-297.
Black et al., "C-Reactive Protein", The Journal of Biological Chemistry, vol. 279, No. 47, Nov. 19, 2004, pp. 48487-48490.
Blicharz et al., "Fiber-Optic Microsphere-Based Antibody Array for the Analysis of Inflammatory Cytokines in Saliva", Analytical Chemistry, Mar. 15, 2009, vol. 81, No. 6, pp. 2106-2114.
Born et al., "Principles of Optics: Electromagnetic Theory of Propagation, Interference and Diffraction of Light", Sixth Edition, 1980, pp. 808. [Uploaded in 2 parts].
Braasch et al., "Locked Nucleic Acid (LNA): Fine-Tuning the Recognition of DNA and RNA", Chemistry & Biology, vol. 8, No. 1, pp. 1-7.
Bustamante et al., "Grabbing the Cat by the Tail: Manipulating Molecules One by One", Nature Reviews Molecular Cell Biology, 2000, vol. 1, pp. 130-136.
Calin et al., "MicroRNA-Cancer Connection: The Beginning of a New Tale", Cancer Research, Aug. 1, 2006, vol. 66, No. 15, pp. 7390-7394.
Chan et al., "MicroRNA-21 is an Antiapoptotic Factor in Human Glioblastoma Cells", Cancer Research, Jul. 15, 2005, vol. 65, No. 14, pp. 6029-6033.
Chao et al., "Polymer Microring Resonators for Biochemical Sensing Applications", IEEE Journal of Selected Topics in Quantum Electronics, Jan./Feb. 2006, vol. 12, No. 1, pp. 134-142.
Chavey et al., "Oestrogen Receptor Negative Breast Cancers Exhibit High Cytokine Content", Breast Cancer Research, Jan. 29, 2007, vol. 9, No. 1, pp. 1-11.
Chen et al., "MicroRNAs Modulate Hematopoietic Lineage Differentiation", Science, Jan. 2, 2004, vol. 303, pp. 83-86.

Chen et al., "Real-Time Quantification of MicroRNAs by Stem-Loop RT-PCR", Nucleic Acids Research, 2005, vol. 33, No. 20, pp. 9.
Coutlée et al., "Immunodetection of DNA with Biotinylated RNA Probes: A Study of Reactivity of a Monoclonal Antibody to DNA-RNA Hybrids", Analytical Biochemistry, 1989, vol. 181, No. 1, pp. 96-105.
Dammer et al., "Specific Antigen/Antibody Interactions Measured by Force Microscopy", Biophysical Journal, Vol0 70, May 1996, pp. 2437-2441.
De Vos et al., "SOI Optical Microring Resonator with Poly(ethylene glycol) Polymer Brush for Label-Free Biosensor Applications", Biosensors and Bioelectronics, Apr. 15, 2009, vol. 24, No. 8, pp. 2528-2533.
Dirksen et al., "Rapid Oxime and Hydrazone Ligations with Aromatic Aldehydes for Biomolecular Labeling", Bioconjugate Chemistry, Dec. 2008, vol. 19, No. 12, pp. 2543-2548.
Dobbs et al., "Caution! Piranha solutions are extraordinarily dangerous, reacting explosively with trace quantities of organics", Chemical & Engineering News, Apr. 23, 1990, p. 2.
Durand et al., "A 275 Basepair Fragment at the 5' End of the Interleukin 2 Gene Enhances Expression from a Heterologous Promoter in Response to Signals from the T Cell Antigen Receptor", Journal of Experimental Medicine, Feb. 1987, vol. 165, pp. 395-407.
Elayadi et al., "Application of PNA and LNA Oligomers to Chemotherapy", Current Opinion in Investigational Drugs, 2001, vol. 2, No. 4, pp. 558-561.
Fan et al., "Sensitive Optical Biosensors for Unlabeled Targets: a Review", Analytica Chimica Acta, Jul. 14, 2008, vol. 620, No. 1-2, pp. 8-26.
Fang et al., "Attomole Microarray Detection of microRNAs by Nanoparticle-Amplified SPR Imaging Measurements of Surface Polyadenylation Reactions", Journal of the American Chemical Society, Nov. 1, 2006, vol. 128, No. 43, pp. 14044-14046.
Fineberg et al., "MicroRNAs Potentiate Neural Development", Neuron, Nov. 12, 2009, vol. 64, No. 3, pp. 303-309.
Friedman et al., "Most Mammalian mRNAs are Conserved Targets of MicroRNAs", Genome Research, Jan. 2009, vol. 19, No. 1, pp. 92-105.
Fujita et al., "Cytokine Profiling of Prostatic Fluid from Cancerous Prostate Glands", Prostate, Jun. 1, 2008, vol. 68, No. 8, pp. 872-882.
Gangaraju et al., "MicroRNAs: Key Regulators of Stem Cells", Nature Reviews Molecular Cell Biology, Feb. 2009, vol. 10, No. 2, pp. 116-125.
Gebert et al., "*Helicobacter Pylori* Vacuolating Cytotoxin Inhibits T Lymphocyte Activation", Science, Aug. 22, 2003, vol. 301, pp. 1099-1102.
Giesler et al., "Bean Pod Mottle Virus: A Threat to U.S. Soybean Production", Plant Disease, 2002, vol. 86, No. 12, pp. 1280-1289.
Goodman, Joseph W., "Introduction to Fourier Optics", 3rd Edition, 2004, pp. 491. [Uploaded in 2 parts].
Hecht, Eugene, "Optics", 4th Edition, Adelphi University, Addison-Wesley, 2002, pp. 698. [Uploaded in 2 parts].
Hornstein et al., "The MicroRNA miR-196 acts Upstream of Hoxb8 and Shh in Limb Development", Nature, Dec. 1, 2005, vol. 438, pp. 671-674.
Horowitz et al., "The Art of Electronics", 2nd Edition, Cambridge University Press, 1989, pp. 1125. [Uploaded in 4 Parts].
Hu et al., "An Antibody-Based Microarray Assay for Small RNA Detection", Nucleic Acids Research, 2006, vol. 34, No. 7, e52, pp. 7.
Hutvagner et al., "A Cellular Function for the RNA-Interference Enzyme Dicer in the Maturation of the let-7 Small Temporal RNA", Science, Aug. 3, 2001, vol. 293, pp. 834-838.
Invitrogen, "Fetal Bovine Serum—Qualified", Invitrogen Cat# 26140, 2009, pp. 6, http://tools.invitrogen.com/contents/sfs/productnotes/F_FBS%20Qualified%20RD-MKT-TL-HL0506021.pdf.
Jackson, "Classical Electrodynamics", Third Edition, John Wiley & Sons, Inc., 1998, pp. 832. [Uploaded in 3 Parts].
Jang et al., "Optical Fiber SPR Biosensor with Sandwich Assay for the Detection of Prostate Specific Antigen", Optics Communications, Jul. 15, 2009, vol. 282, No. 14, pp. 2827-2830.

(56) References Cited

OTHER PUBLICATIONS

Kaur et al., "Thermodynamic, Counterion, and Hydration Effects for the Incorporation of Locked Nucleic Acid Nucleotides into DNA Duplexes", Biochemistry, 2006, vol. 45, No. 23, pp. 7347-7355.

Kim et al., "Preparation of Multivesicular Liposomes", Biochimica et Biophysica Acta (BBA)—Biomembranes, Mar. 9, 1983, vol. 728, No. 3, pp. 339-348.

Kinney et al., "Monoclonal Antibody Assay for Detection of Double-Stranded RNA and Application for Detection of Group A and Non-Group A Rotaviruses", Journal of Clinical Microbiology, Jan. 1989, vol. 27, No. 1, pp. 6-12.

Koshkin et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition", Tetrahedron, vol. 54, No. 14, Apr. 2, 1998, pp. 3607-3630.

Krönke et al., "Sequential Expression of Genes Involved in Human T Lymphocyte Growth and Differentiation", Journal of Experimental Medicine, Jun. 1985, vol. 161, pp. 1593-1598.

Kumar et al., "The First Analogues of LNA (Locked Nucleic Acids): Phosphorothioate-LNA and 2'-thio-LNA", Bioorganic & Medicinal Chemistry Letters, vol. 8, No. 16, Aug. 18, 1998, pp. 2219-2222.

Lee et al., "Direct Measurement of the Forces Between Complementary Strands of DNA", Science, Nov. 4, 1994, vol. 266, No. 5186, pp. 771-773.

Lee et al., "MicroRNA Maturation: Stepwise Processing and Subcellular Localization", The EMBO Journal, 2002, vol. 21, No. 17, pp. 4663-4670.

Lee et al., "The C. Elegans Heterochronic Gene lin-4 Encodes Small RNAs with Antisense Complementarity to lin-14", Cell, Dec. 3, 1993, vol. 75, pp. 843-854.

Lee et al., "The Nuclear RNase III Drosha Initiates MicroRNA Processing", Letters to Nature, Sep. 25, 2003, vol. 425, pp. 415-419.

Li et al., "Real-Time Polymerase Chain Reaction MicroRNA Detection Based on Enzymatic Stem-Loop Probes Ligation", Analytical Chemistry, 2009, vol. 81, No. 13, pp. 5446-5451.

Lieberman et al., "Pharmaceutical Dosage Forms: Disperse Systems", Marcel Dekker Inc, Monticello, New York, U.S.A., 1988, Ch. 8, pp. 285-366.

Lim et al., "Microarray Analysis Shows that some MicroRNAs Downregulate Large Numbers of Target mRNAs", Nature, Feb. 17, 2005, vol. 433, pp. 769-773.

Lin et al., "Myc-Regulated MicroRNAs Attenuate Embryonic Stem Cell Differentiation", The Embo Journal, 2009, vol. 28, pp. 3157-3170.

Little et al., "Microring Resonator Channel Dropping Filters," Journal of Lightwave Technology, Jun. 1997, vol. 15, No. 6, pp. 998-1005.

Lu et al., "MicroRNA Expression Profiles Classify Human Cancers", Nature, Jun. 9, 2005, vol. 435, pp. 834-838.

Mandal et al., "A Multiplexed Optofluidic Biomolecular Sensor for Low Mass Detection", Lab on a Chip, 2009, vol. 9, pp. 2924-2932.

Manger et al., "Differential Effect of Cyclosporin A on Activation Signaling in Human T Cell Lines", Journal of Clinical Investigation, May 1986, vol. 77, No. 5, pp. 1501-1506.

Marty et al., "Nonlinear Analyte Concentration Gradients for One-Step Kinetic Analysis Employing Optical Microring Resonators", Analytical Chemistry, Jul. 3, 2012, vol. 84, No. 13, pp. 5556-5564.

Mazur et al., "Concentration of IL-2, IL-6, IL-8, IL-10 and TNF-Alpha in Children with Acute Lymphoblastic Leukemia After Cessation of Chemotherapy", Hematological Oncology, 2004, vol. 22, No. 1, pp. 27-34.

McClellan et al., "Label-Free Virus Detection Using Arrays of Silicon Photonic Microring Resonators", Biosensors & Bioelectronics, Jan. 15, 2012, vol. 31, pp. 388-392.

Meola et al., "MicroRNAs and Genetic Diseases", PathoGenetics, 2009, vol. 2, No. 7, pp. 1-14.

Mudumba et al., "Photonic Ring Resonance is a Versatile Platform for Performing Multiplex Immunoassays in Real Time", Journal of Immunological Methods, 2017, vol. 448, pp. 34-43.

Murchison et al., "miRNAs on the Move: miRNA Biogenesis and the RNAi Machinery", Current Opinion in Cell Biology, Jun. 2004, vol. 16, No. 3, pp. 223-229.

Nelson et al., "Microarray-Based, High-Throughput Gene Expression Profiling of MicroRNAs", Nature Methods, Nov. 2004, vol. 1, No. 2, pp. 155-161.

Nicoloso et al., "MicroRNAs—The Micro Steering Wheel of Tumour Metastases", Nature Reviews Cancer, 2009, pp. 9.

Nicoloso et al., "MicroRNAs: New Players in AML Pathogenesis", Cancer Treatment and Research, Jan. 1, 2010, vol. 145, pp. 169-181.

O'Hara et al., "Cell-Surface and Cytokine Biomarkers in Autoimmune and Inflammatory Diseases", Drug Discovery Today, Apr. 2006, vol. 11, No. 7-8, pp. 342-347.

Ohtsuka et al., "Joining of Synthetic Ribotrinucleotides with Defined Sequences Catalyzed by T4 Rna Ligase", European Journal of Biochemistry, 1977, vol. 81, No. 2, pp. 285-291.

Ørom et al., "MicroRNA-10a Binds the 5'UTR of Ribosomal Protein mRNAs and Enhances Their Translation", Molecular Cell, May 23, 2008, vol. 30, 460-471.

Orsilles et al., "IL-2 and IL-10 Serum Levels in HIV-1-Infected Patients with or Without Active Antiretroviral Therapy", APMIS, Jan. 2006, vol. 114, No. 1, pp. 55-60.

Ørum et al., "Locked Nucleic Acids: A Promising Molecular Family for Gene-Function Analysis and Antisense Drug Development", Current Opinion in Molecular Therapeutics, Jun. 2001, vol. 3, No. 3, pp. 239-243.

Poethig, R. Scott, "Small RNAs and Developmental Timing in Plants", Current Opinion in Genetics & Development, Aug. 2009, vol. 19, No. 4, pp. 374-378.

Poy et al., "A Pancreatic Islet-Specific MicroRNA Regulates Insulin Secretion", Nature, 2004, vol. 432, No. 7014, pp. 226-230.

Roberts, Peter, "MicroRNA Expression Profiling on Arrays Enhanced with Locked Nucleic Acids", Nature Methods, Exiqon, Apr. 2006, pp. iii-iv.

Rockwell et al., "A COX-2 Metabolite of the Endogenous Cannabinoid, 2-Arachidonyl Glycerol, Mediates Suppression of IL-2 Secretion in Activated Jurkat T Cells", Biochemical Pharmacology, Aug. 1, 2008, vol. 76, No. 3, pp. 353-361.

Romaniuk et al., "The Effect of Acceptor Oligoribonucleotide Sequence on the $T_4$ RNA Ligase Reaction", European Journal of Biochemistry, 1982, vol. 125, pp. 639-643.

Scheler et al., "Label-Free, Multiplexed Detection of Bacterial tmRNA Using Silicon Photonic Microring Resonators", Biosensors & Bioelectronics, 2012, vol. 36, No. 1, pp. 56-61.

Schratt et al., "A Brain-Specific MicroRNA Regulates Dendritic Spine Development", Nature, Jan. 19, 2006, vol. 439, No. 7074, pp. 283-289.

Schwelb, Dr. Otto, "The Vernier Principle in Photonics", Concordia University, published May 6, 2011, pp. 4.

Sempere et al., "Expression Profiling of Mammalian MicroRNAs Uncovers a Subset of Brain-Expressed MicroRNAs with Possible Roles in Murine and Human Neuronal Differentiation", Genome Biology, Article R13, 2004, vol. 5, No. 3, pp. 11.

Shi, Yang, "Mammalian RNAi for the Masses", Trends in Genetics, Jan. 2003, vol. 19, No. 1, pp. 9-12.

Shia et al., "Single Domain Antibodies for the Detection of Ricin Using Silicon Photonic Microring Resonator Arrays", Analytical Chemistry, Jan. 2013, vol. 85, No. 2, pp. 805-810.

Shopova, "On-Column Micro-Gas-Chromatography Detection with Capillary Based Optical Ring Resonators", Analytical Chemistry, 2008, vol. 80, pp. 2232-2238.

Siegman, Anthony E., "Lasers", University Science Books, 1986, pp. 1283. [Uploaded in 7 parts].

Sigma®, "Product Information", p. 1585 Datasheet, Sigma-Aldrich, Inc., 2002, https://www.sigmaaldrich.com/content/dam/sigma-aldrich/docs/Sigma/Datasheet/4/p1585dat.pdf, p. 1.

Singh et al., "Synthesis of 2'-Amino-LNA: A Novel Conformationally Restricted High-Affinity Oligonucleotide Analogue with a Handle", The Journal of Organic Chemistry, 1998, vol. 63, No. 26, pp. 10035-10039.

Sípová et al., "Surface Plasmon Resonance Biosensor for Rapid Label-Free Detection of Microrna at Subfemtomole Level", Analytical Chemistry, Dec. 15, 2010, vol. 82, No. 24, pp. 10110-10115.

(56) References Cited

OTHER PUBLICATIONS

Sloan et al., "Interfacing Lipid Bilayer Nanodiscs and Silicon Photonic Sensor Arrays for Multiplexed Protein-Lipid and Protein-Membrane Protein Interaction Screening", Analytical Chemistry, Mar. 5, 2013, vol. 85, No. 5, pp. 2970-2976.
Smith, K.A., "Interleukin-2: Inception, Impact, and Implications", Science, May 27, 1988, vol. 240, No. 4856, pp. 1169-1176.
Solulink, https://web.archive.org/web/20100719122056/http://www.solulink.com/, as archived Jul. 19, 2010, pp. 2.
Streit et al., "Northern Blot Analysis for detection and Quantification of RNA in Pancreatic Cancer Cells and Tissues", Nature Protocols, 2009, vol. 40, No. 1, pp. 37-43.
Sundrud et al., "Inhibition of Primary Human T Cell Proliferation by *Helicobacter Pylori* Vacuolating Toxin (VacA) is Independent of VacA Effects on IL-2 Secretion", Proceedings of the National Academy of Sciences of the United States of America (PNAS), May 18, 2004, vol. 101, No. 20, 7727-7732.
Suter et al., "Label-Free Quantitative DNA Detection Using the Liquid Core Optical Ring Resonator", Biosensors and Bioelectronics, Feb. 28, 2008, vol. 23, No. 7, pp. 1003-1009.
Székvölgyi et al., "Ribonucleoprotein-Masked Nicks at 50-kbp Intervals in the Eukaryotic Genomic DNA", Proceedings of the National Academy of Sciences of the United States of America (PNAS), Sep. 18, 2007, vol. 104, No. 38, pp. 14964-14969.
Szoka, Jr., Francis, "Comparative Properties and Methods of Preparation of Lipid Vesicles (Liposomes)", Annual Review of Biophysics and Bioengineering, 1980, vol. 9, pp. 467-508.
Tsai et al., "MicroRNAs in Common Diseases and Potential Therapeutic Applications", Clinical and Experimental Pharmacology and Physiology, 2010, vol. 37, No. 1, pp. 102-107.
Varkonyi-Gasic et al., "Protocol: a Highly Sensitive RT-PCR Method for Detection and Quantification of MicroRNAs", Plant Methods, 2007, vol. 3, pp. 12.
Veeramachaneni et al., "Analysis of Forces Acting on Superparamagnetic Beads in Fluid Medium in Gradient Magnetic Fields", Excerpt from the Proceedings of the COMSOL Conference 2009 Boston, pp. 5.
Vollmer et al., "Single Virus Detection from the Reactive Shift of a Whispering-Gallery Mode", Proceedings of the National Academy of Sciences of the United States of America (PNAS), Dec. 30, 2008, vol. 105, No. 52, pp. 20701-20704.
Wang et al., "Cell Cycle Regulation by MicroRNAs in Embryonic Stem Cells", Cancer Research, May 15, 2009, vol. 69, No. 10, pp. 4093-4096.
Watercampws, https://web.archive.org/web/20100614031023/http://watercampws.uiuc.edu/waterclear/labs/, as archived Jun. 14, 2010, pp. 2.
Weiss et al., "The Role of T3 Surface Molecules in the Activation of Human T Cells: A Two-Stimulus Requirement for IL 2 Production Reflects Events Occurring at a Pre-Translational Level", The Journal of Immunology, Jul. 1984, vol. 133, No. 1, pp. 123-128.
White et al., "Label-Free Detection with the Liquid Core Optical Ring Resonator Sensing Platform", Methods in Molecular Biology, 2009, vol. 503, pp. 139-165.
Wu et al., "Multiple MicroRNAs Modulate p21Cip1/Waf1 Expression by Directly Targeting its 3' Untranslated Region", Oncogene, 2010, vol. 29, pp. 2302-2308.
Xu et al., "Folded Cavity SOI Microring Sensors for High Sensitivity and Real Time Measurement of Biomolecular Binding", Optics Express, Sep. 15, 2008, vol. 16, No. 19, pp. 15137-15148.
Yang et al., "Detection of Picomolar Levels of Interleukin-8 in Human Saliva by SPR", Lab on a Chip, Oct. 2005, vol. 5, No. 10, pp. 1017-1023.
Yang et al., "Direct, Electronic MicroRNA Detection for the Rapid Determination of Differential Expression Profiles", Angewandte Chemie International Edition, 2009, vol. 48, pp. 5.
Young et al., "Cytokine Multiplex Analysis", Inflammation and Cancer, Methods in Molecular Biology, 2009, Ch. 4, vol. 511, pp. 85-105.
Zhu et al., "A Microdevice for Multiplexed Detection of T-Cell-Secreted Cytokines", Lab on a Chip, Dec. 2008, vol. 8, pp. 2197-2205.
Zhu et al., "Opto-Fluidic Micro-Ring Resonator for Sensitive Label-Free Viral Detection", Analyst, 2008, vol. 133, pp. 356-360.
Zhu et al., "Rapid and Label-Free Detection of Breast Cancer Biomarker CA15-3 in Clinical Human Serum Samples with Optofluidic Ring Resonator Sensors", Analytical Chemistry, 2009, vol. 81, No. 24, pp. 9858-9865.

\* cited by examiner

| A | T | G | A | C | T | ... |

FIG. 5a

| A | B | C | B | T | B | G | B | A | ... |

FIG. 5b

| P | A | RP | P | C | RP | P | ... |

FIG. 5c

| A+P | RP | M | C+P | RP | M | ... |

FIG. 5d

LABEL-FREE OPTICAL SENSORS

PRIORITY CLAIM AND RELATED PATENT APPLICATION

This document claims priority from U.S. Provisional Patent Application Ser. No. 61/005,372 entitled "Method and Apparatus for Clocked Synthesis of Genetic Matter" and filed on Dec. 6, 2007, the entire contents of which are incorporated herein by reference as part of the disclosure of this document.

BACKGROUND

This document relates to label-free sensing of chemical and biological materials and applications of such label-free sensing.

Various sequencing techniques use a label to attach to a molecule and the labeled molecule is monitored and interrogated to identify which base has been added or removed from a strand of nucleic acid (NA). Such labeling can be achieved by various labeling techniques, including molecular labeling based on radioactivity, fluorescence, and chemiluminescence. However, a label may cause undesired effects, such as altering the molecular binding kinetics, interfering with the accuracy of the reaction, and limiting the length of a contiguous readout, and may require multiple readouts to construct a high confidence sequence. In addition, molecular labeling may require numerous processing steps such as label attachment, washing, label removal, scanning, etc. and thus could complicate the process, require extended time for processing and add significant cost.

SUMMARY

Techniques, apparatus and system are described to provide label free sensors used to monitor enzymatic processes. Such label free sensors can be used to detect sequencing of nucleic acid, for example.

In one aspect, a label-free enzymatic process monitoring system includes an array of label-free optical sensors to detect an optical signal in response to modification of one or more target genetic structures by addition of a base by synthesis. Each label-free optical sensor is functionalized with a respective target genetic structure. The system includes a fluid flow control module that includes fluid receiving units to provide paths for different fluids to flow into the fluid flow control module. The fluid flow control module includes at least one switch connected to the fluid receiving units to selectively switch among the fluid receiving units to receive a select sequence of the fluids through the fluid receiving units. The select sequence the fluids includes at least a nucleotide base or deoxyribonucleoside 5'-triphosphate (dNTP). A fluid channel is connected between the fluid flow control module and the array of label-free sensors to allow the select sequence of the fluids to flow from the fluid flow control module to the array of label-free optical sensors.

Implementations can optionally include one or more of the following features. The array of label-free optical sensors can include an optical evanescent field sensor to hold the respective target genetic structure within an evanescent field. The label-free optical evanescent field sensor can include a resonant cavity. The resonant cavity can include a ring resonator cavity. The array of label-free optical sensors can measure a shift in a resonant frequency of the resonant cavity. The array of label-free optical sensors can measure a change in a complex refractive index of the resonant cavity. The fluid flow control module can provide a single species of dNTP or nucleotide to the array of label-free optical sensors. The fluid flow control module can provide a reagent for modifying the target genetic structure to the array of sensors. The array of label-free optical sensors can detect the optical signal while adding the nucleotide base.

In another aspect, sequencing nucleic acids includes functionalizing a surface of a label-free optical sensor with unknown species of nucleic acid. A reagent comprising synthesis materials and a known nucleotide base is selectively introduced to the unknown species of nucleic acid. A change in an output signal of the label-free optical sensor is measured to detect synthesis of the nucleic acid when a nucleotide base in the unknown species of nucleic acid reacts with the known dNTP or nucleotide base. A next nucleotide base in the unknown nucleic acid to react is identified based on the introduced known dNTP or nucleotide base and the measured change in the output signal.

Implementations can include one or more of the following features. A magnitude of the output signal can be measured to determine a number of the introduced known nucleotide base incorporated during the detected synthesis. The label-free optical sensor that includes an optical resonator can be used to monitor the synthesis process occurring within an optical field of the resonator. The unknown species of nucleic acid can be amplified using a selectively bound primer and hybridization sequences. Solid phase amplification and hybridization of the unknown species of nucleic acid can be performed in parallel. An amount of the unknown species of nucleic acid can be measured based on the output signal of the optical sensor before and after functionalization. A known sequence of nucleotide bases can be applied and inadvertently or non-selectively bound materials can be removed by applying a washing agent between the nucleotide bases. The surface of the optical sensor can be functionalized with a single species of nucleic acid based on the output signal of the optical sensor. Measuring a change in an output signal of the label-free optical sensor can include: measuring an output signal of the label-free optical sensor before introducing the known nucleotide base; measuring another output signal of the label-free optical sensor after introducing the known nucleotide base; and identifying a difference between the measured output signals. The unknown species of nucleic acid can be held within an evanescent field.

Yet in another aspect, monitoring an enzymatic process within an optical field of a label-free optical resonator includes detecting an optical signal from the label-free optical resonator in response to an application of one or more enzymes to identify an enzymatic process that results in a modification of the nucleic acid. The enzymatic process can include one of the following reactions: polymerase driven base extension; polymerase repair activity driven base excision; reverse transcriptase driven DNA extension; reverse transcriptase driven RNA exonuclease activity; DNA cleavage driven by site specific endonuclease activity; annealing driven by ligase enzyme activity and or topoisomerase action and or recombination enzymes; phosphorylation driven by kinase; dephosphorylation driven by phosphatase; RNA Splicing driven by splicing enzymes and or catalytic RNA splicing fragments; and cleavage through miRNA driven DICER complex.

Yet in another aspect, a label-free enzymatic process monitoring system can include an array of label-free optical sensors to detect an optical signal in response to modification of one or more target genetic structures. Each label-free optical sensor holds a respective target genetic structure within an evanescent field. The system includes a fluid flow control module to receive one or more fluids comprising a reagent to modify the one or more target genetic structure. A fluid channel is connected between the fluid flow control module and the array of label-free sensors to allow the one or more fluids to flow from the fluid flow control module to the array of label-free optical sensors.

The techniques, apparatus and system as described in this specification can potentially provide one or more of the following advantages. For example, the amount of target material on a sensor can be measured to allow accurate calibration of the amount on the sensor. Also, the system can evaluate when the addition of a base has run to completion. To speed the synthesis reaction rate, real time monitoring of the reaction can be performed. In addition, the real time incorporation of bases in a sequence extension reaction can be performed based on small sensor size and high sensitivity.

BRIEF DESCRIPTION OF THE DRAWINGS

FIGS. 5a-d illustrate several options for sequence of the different solutions which can be applied over the sensors.

Figure 1:
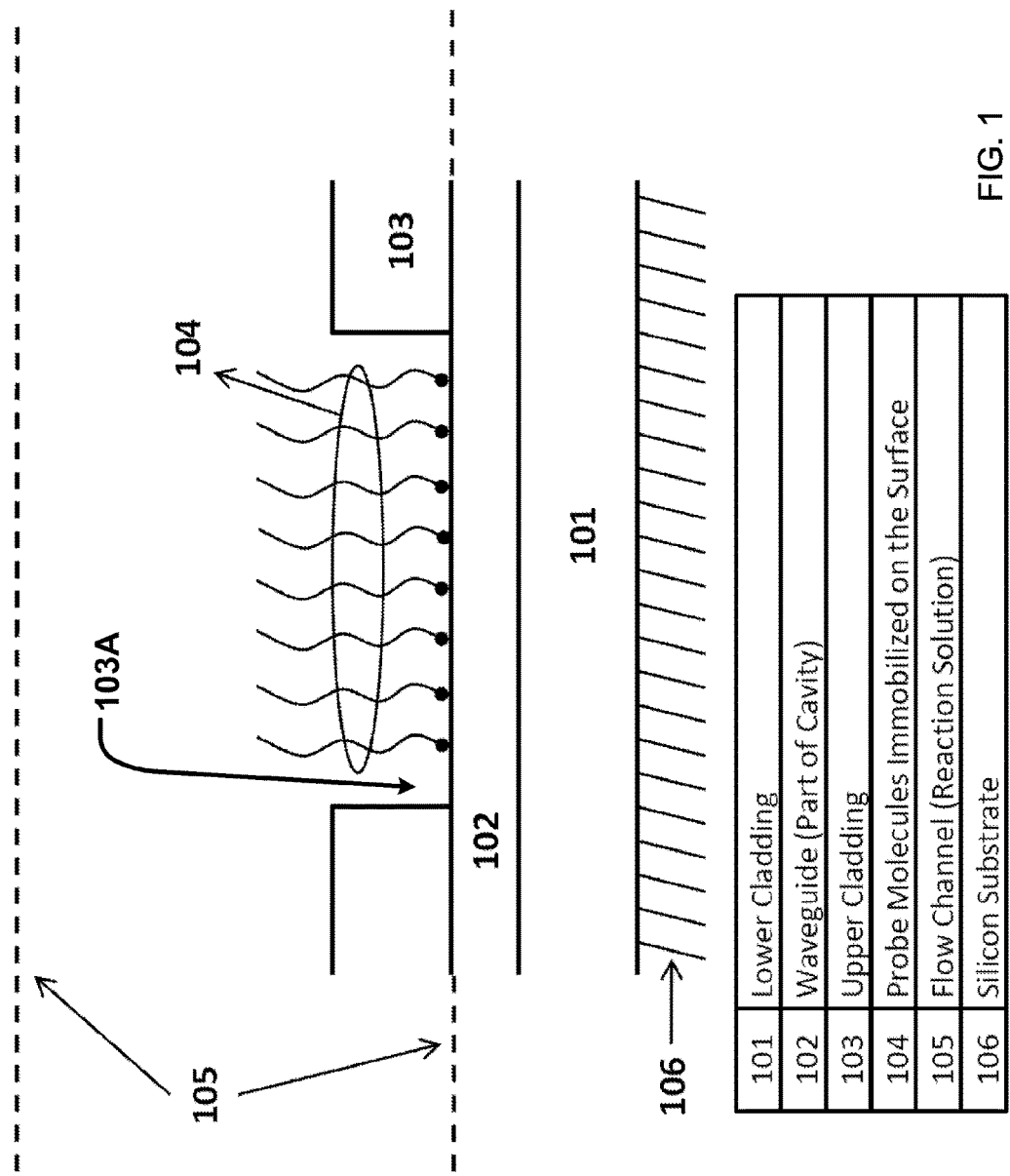
FIG. 1 illustrates a cross-section of an exemplary optical evanescent field sensor suitable for sequencing applications.

These fluid options and sequences are for illustrative purposes, and can be combined in ways that employ one or more of these approaches in a variety of different orders and combinations.

DETAILED DESCRIPTION

Label-free techniques can provide molecular sensing and detection without using a molecular label. Such label-free techniques can be used to mitigate certain undesired effects in molecular labeling. For example, time consuming and potentially side-effect causing label-related process steps can be eliminated. In particular, label-free techniques can be used to run a synthesis reaction at a substantially higher rate than that of a synthesis reaction based on molecular labeling. As such, the processing time of a label-free technique may be reduced to a time determined by the kinetics of the synthesis reaction. For example, a label-free technique may be used to reduce the time from 10 s of minutes per read in a system based on molecular labeling down to seconds, or even milliseconds per base call.

Techniques, systems and apparatus as described in this specification can be used to provide label-free sensors for monitoring enzymatic processes, such as synthesis of genetic material. A resonant cavity with an evanescent field can be used to sequence an unknown nucleic acid sequence without labels. In one aspect, genetic material is held within the evanescent field of the resonant cavity and chemical precursors for the extension of nucleic acid base pairs are added repetitively in sequence. The sensor is interrogated synchronously with the addition of each subsequent nucleic acid based. A change in the resonant cavity properties that corresponds to the addition of a particular base indicates incorporation into the synthesis product and indicates the next corresponding base.

Examples of label-free techniques, systems and apparatus are described below for sequencing a nucleic acid. For example, a label-free sequencing apparatus can include one or more label-free sensors for sensing a biological and chemical material, a mechanism for holding a nucleic acid in interaction with a label-free sensor, a means for controllably introducing a reagent and components for modification of the nucleic acid, and a label-free means for interrogating the one or more label-free sensors to obtain output from the one or more label-free sensors and evaluating whether a nucleic acid in interaction with a sensor is modified. Such a label-free sensor may be implemented to achieve a limit of detection at or below the addition of a single base.

As a specific example, such a label-free sensor can be implemented by using an optical sensor that monitors the physical presence of a base via detection of the optical evanescent wave to determine synthesis, and does not require a label attached to the base. In the above exemplary apparatus, a nucleic acid is placed in the optical evanescent field of a label-free optical sensor. In another example, a method for sequencing nucleic acids can be implemented based on one or more label-free optical sensors. In this method, a nucleic acid species is placed within the range of an optical evanescent field sensor and a reagent containing synthesis materials and a known dNTP or base are introduced to the bound species. The output from the optical evanescent field sensor is monitored to measure a change and the measured change is used to determine whether synthesis has occurred. This method also includes determining the next base in sequence based on knowledge of which dNTP or base is present at the time a sensor signal from the optical evanescent field sensor indicates the presence of an additional bound matter.

In one implementation of a label-free sequencing apparatus, an optical sensor is placed on a substrate in such a manner that the optical sensor can be interrogated while simultaneously allowing a reaction to occur in the sensing region of the optical sensor. The optical sensor can be implemented using an evanescent field sensor. Examples of an evanescent field sensor include: resonant cavities, Mach-Zehnder interferometers, or other applicable interferometers with a sensing mechanism that involves a change in the complex refractive index in the optical path. One example is a ring resonator, which can be addressed using waveguides that are routed out of the sensing region.

An optical ring resonant cavity forms a closed-loop waveguide. In the optical ring resonant cavity, light propagates in the form of whispering gallery modes (WGMs) that result from the total internal reflection of the light along the curved surface of the ring. The WGM is a surface mode that circulates along the ring resonator surface and interacts repeatedly with any material (e.g., target genetic material) on the surface through the WGM evanescent field. Unlike a straight waveguide sensor, the effective light-material interaction length of a ring resonator sensor is no longer determined by the sensor's physical size, but rather by the number of revolutions of the light supported by the resonator, which is characterized by the resonator quality factor, or the Q-factor. The effective length $L_{eff}$ is related to the Q-factor by equation 1 below.

$$L_{eff} = \frac{Q\lambda}{2\pi n} \quad (2)$$

Where λ is wavelength and n is the refractive index of the ring resonator. Due to the large Q-factor, the ring resonant cavity can provide sensing performance superior to a straight waveguide sensor while using orders of magnitude less surface area and sample volume. In addition, the small size of the ring resonator allows an implementation of a larger number of ring resonant cavities in an array of sensors.

An optical sensor on a substrate can be fabricated using a lithographic technique. Bounding the optical sensor to a substrate can provide a convenient means to handle the optical sensor and to fabricate multiple sensors in arrays. In other designs, an optical sensor may be detached from a substrate and be free floating.

FIG. 1 illustrates a cross-section of an exemplary optical evanescent field sensor suitable for sequencing applications. This sensor includes an optical resonator or an optical interferometric structure that includes a waveguide 102 formed on a substrate 106 which may be, for example, a silicon substrate. A first, lower cladding layer 101 with an index less than that of the waveguide 102 is formed on the substrate 106 and is located beneath the waveguide 102. A second, upper cladding layer 103 is formed over the waveguide 102 and has an index less than that of the waveguide 102. The upper cladding layer 103 is patterned to have one or more regions 103A in which the cladding material for the upper cladding layer 103 is removed to form a sensing region 103A. The sensing region is structured to either completely expose a section of the waveguide 102 or to have a thin layer of the cladding material, to allow a sufficient amount of the optical evanescent field of the guided light in the waveguide 102 to be present in the sensing region 103A. A genetic material 104 (e.g., DNA, RNA, LNA, etc.) is deposited on a surface via a functionalizing process in the sensing region 103A in proximity to the waveguide 102, in such a manner that the evanescent field of the waveguide 102 can interact with the genetic material 104. Cladding regions in the upper cladding layer 103 are shown to define one exemplary sensing region 103A that determines which portion of the waveguide 102 is to be functionalized with the genetic material 104. A flow channel or fluidic cavity 105 is formed on top of the sensor and a fluidic control mechanism is provided to direct different solutions into the flow channel or fluidic cavity 105 during a sequencing process for synthesizing a target genetic structure, such as a single species nucleic acid in a sensing region 103A. In addition, the fluidic control mechanism can direct the solutions into the flow channel or fluidic cavity 105 for other enzymatic processes.

Figure 2:
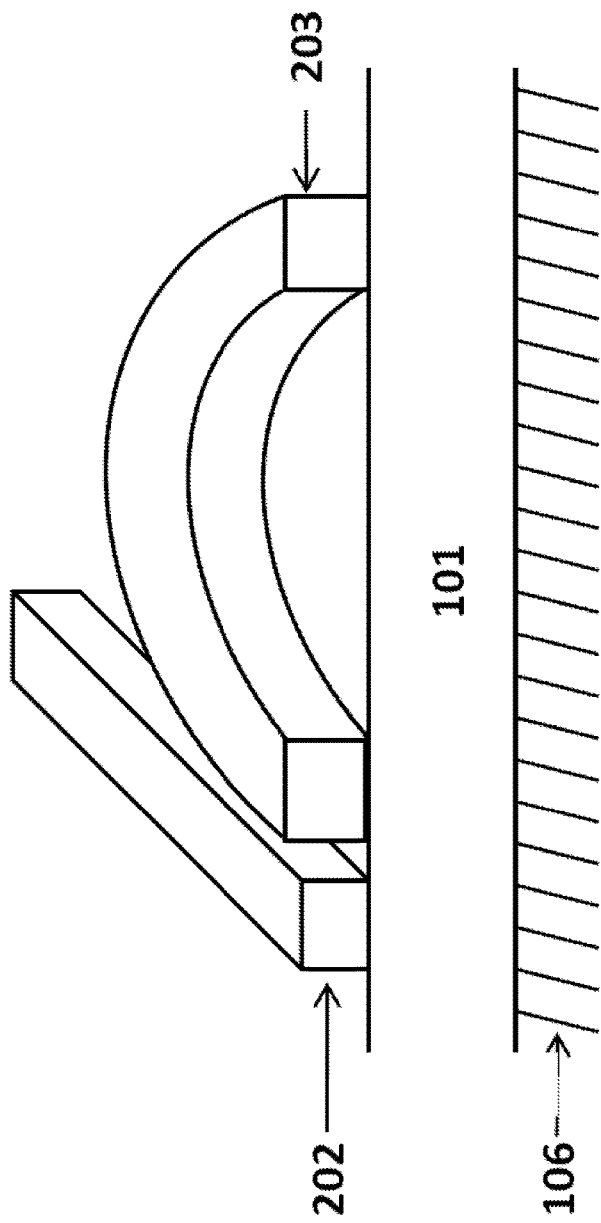
FIG. 2 illustrates a perspective cross section of another example of an optical sensor having a ring resonator cavity and a coupling waveguide, formed on a silicon substrate.

FIG. 2 illustrates a perspective cross section of another example of an optical evanescent field sensor having a ring resonator cavity 203 and a coupling waveguide 202, formed on a silicon substrate 106. The waveguides 202 and 203 are displaced from the substrate via a buried insulator layer 101 as the lower cladding layer, which may be, for example, silicon dioxide. Functionalization can occur in proximity to the surface(s) of the ring resonator cavity 203. In one implementation, similar to the design in FIG. 1, an upper cladding layer over the ring resonator cavity 203 can be patterned to form sensing regions in proximity to the surface of the ring resonator cavity 203 for the synthesis of a target genetic structure, such as a substantially single species nucleic acid.

Figure 3A:
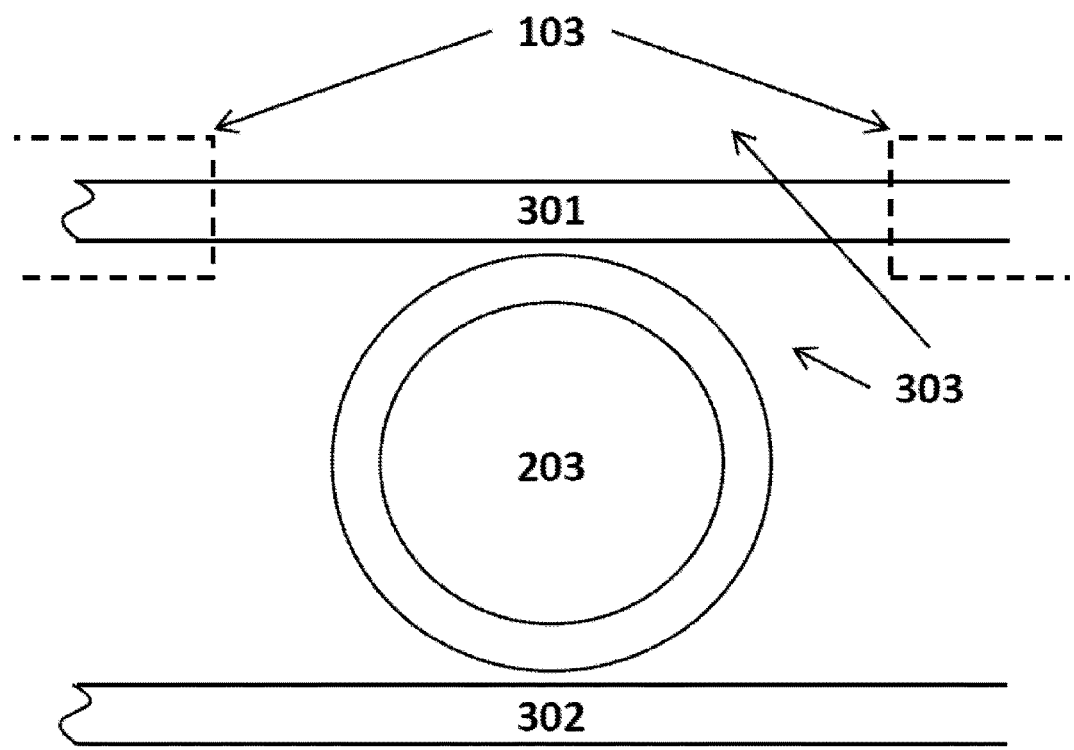
FIG. 3a illustrates a top down view of another example of an optical sensor that includes a ring resonator cavity and two coupling waveguides in evanescent coupling to the ring resonator cavity.
Figure 3B:
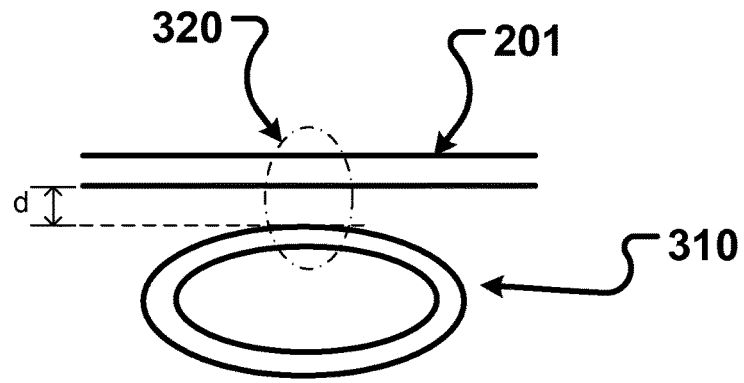
FIGS. 3b-3d illustrate examples of non-circular shaped ring resonant cavities.
Figure 3C:
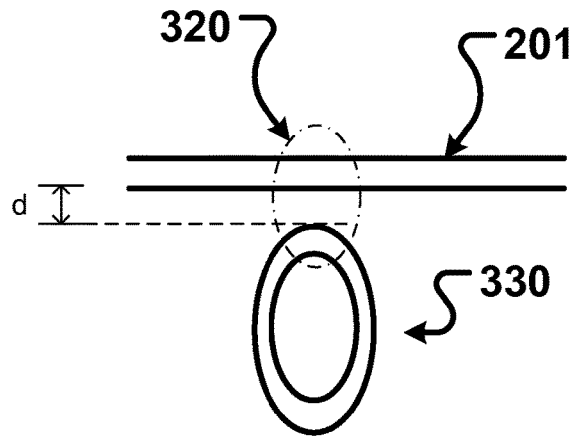
Figure 3D:
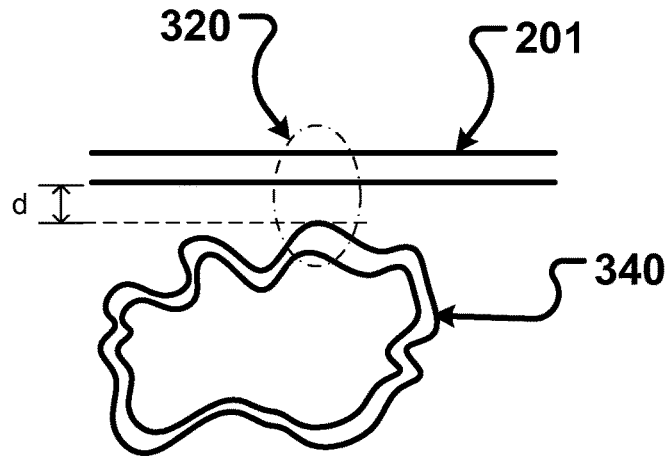

FIG. 3a illustrates a top down view of another example of an optical evanescent field sensor that includes a ring resonator cavity 203 and two coupling waveguides 301 and 302 in evanescent coupling to the ring resonator cavity 203. An upper cladding layer 103 is formed over the first waveguide 301 and is patterned to define one or more sensing regions above the first waveguide 301 as shown in FIG. 1. The cladding layer 103 can be used to confine the interaction of the genetic material in each sensing region to be solely to the immediate proximity of the ring 203. The second waveguide 302 is an optical waveguide and may be used to guiding light in connection with the evanescent sensing at a sensing region in the first waveguide 301.

The ring resonant cavity 203 of FIGS. 2 and 3 can be formed by a waveguide in a closed loop in various configurations. In FIG. 3a, the ring resonator cavity is a closed waveguide loop of a circular shape. This circular closed waveguide loop can support one or more whispering gallery modes along the circular path of the closed waveguide loop at and around the outer surface of the circular waveguide and may be independent of the inner surface of the circular waveguide because the whispering gallery mode exists at and around the outer surface of the circular waveguide. The optical input to the ring resonant cavity 203 can be achieved via evanescent coupling between the waveguide 301 and the ring resonant cavity 203 which are spaced from each other. In other implementations, the closed waveguide loop may be in a non-circular shape that does not support a whispering gallery mode. FIGS. 3b, 3c and 3d show example shapes of non-circular ring resonant cavities which operate based on the waveguide modes rather than whispering gallery modes. A waveguide mode is supported by the waveguide structure including both the outer and inner surfaces as the waveguide boundaries and thus is different from a whispering gallery mode. Each ring resonant cavity is spaced from the waveguide 201 by a distance d that is selected to provide desired evanescent coupling. The evanescent coupling configuration is indicated by the numeral 320. One aspect of such a non-circular closed waveguide loop forming the ring resonant cavity is to provide the same evanescent coupling configuration 320 while providing different closed loop waveguides. FIG. 3b and FIG. 3c show a ring resonant cavity in an elliptical shape in a waveguide mode in two different orientations 310 and 320. The specific geometries of the closed waveguide loop can be selected based on the need of a specific sensor design. Race-track shaped closed waveguide loop, for example, may be used. FIG. 3d shows an example where the closed waveguide loop 340 has an irregular shape that can be designed to fit on a chip. A ring resonant cavity may be used to achieve a high Q factor in the ring resonant cavity in part due to re-circulation of the guided optical signal and such a high Q factor can be exploited to achieve a high detection sensitivity in detecting a minute amount of a material on the surface of the ring resonant cavity in a label-free enzymatic process based on optical sensing and monitoring.

Figure 4A:
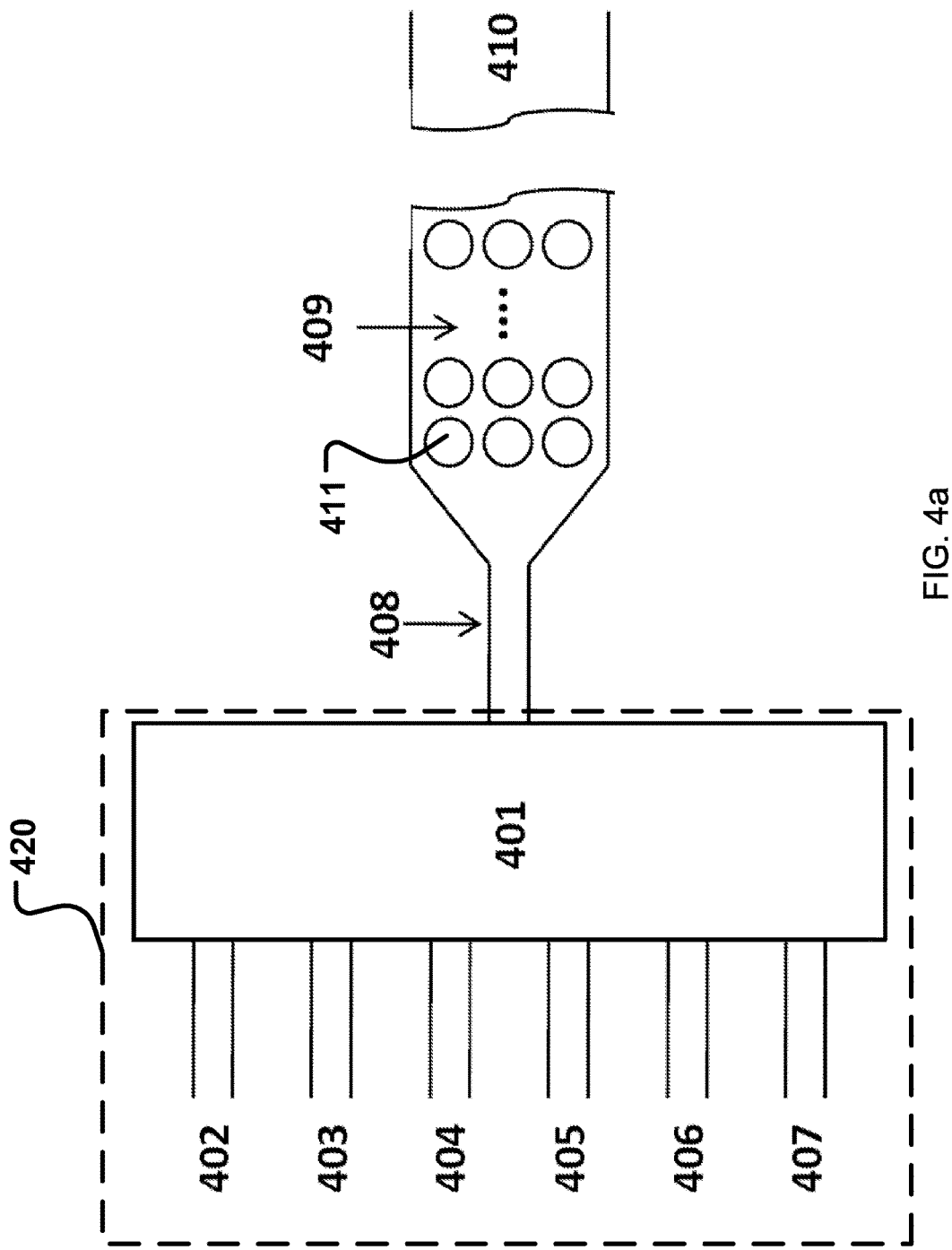
FIG. 4a illustrates a schematic of an example of a synthesis system with a fluid flow control module and a sensor array based on label-free sensors.

FIG. 4a illustrates a schematic of a monitoring system with a fluid flow control module 420 and a sensor array 409 based on label-free sensors. The fluid flow control module 420 includes fluid receiving units, such as ports 402, 403, 404, 405, 406 and 407 to receive various fluid types into the fluid flow control module. Also, one or more switches 401 are provided in the fluid flow control module to selectively switch-in or receive one or more of the fluid types into the fluid flow control module. The sensor array 409 includes a matrix of label-free sensors 411 arranged in various configurations. For example, the label-free sensors 411 can be arranged in a square or rectangular configuration with N number of rows and M number of columns of sensors. The label-free sensors 411 can be arranged in other configurations, such as a circle or a triangle. The label-free sensors 411 may be optical sensors based on the sensor examples in FIGS. 1-3b and other sensor designs.

The fluid flow control module 420 is connected to the sensor array 409 using a flow channel 408. Solutions in the fluid flow control module 420 can flow through the flow channel 408 and arrive at the sensor array 409. Different solutions can be obtained in the fluid flow control module 420 by receiving the various fluid types by using the switch 401, and mixing the received fluids. For example, a mix of the various nucleic acids and the associated synthesis compounds can be added through ports 402-405. In addition, various washing and cleaning solutions, such as buffers can be switched in through ports 406 and 407. The amount and type of fluids to receive and mix in the fluid flow control module 420 can be controlled using the one or more of the switches 401. After the fluids are combined and mixed in a junction region in the fluid flow control module 420, the resultant solution can be applied through the fluid channel 408 and over the sensor array 409. In this configuration, each label-free sensor could have a different unknown sequence attached.

The solution from the fluid flow control module 420 flows over the sensor array 409 and exits the system through the fluid exit 410. Thus, a continuous flow of solutions can be provided across the sensor array 409. In some implementations, the solution can be held static in the sensor array 409 by stopping the flow.

Figure 4B:
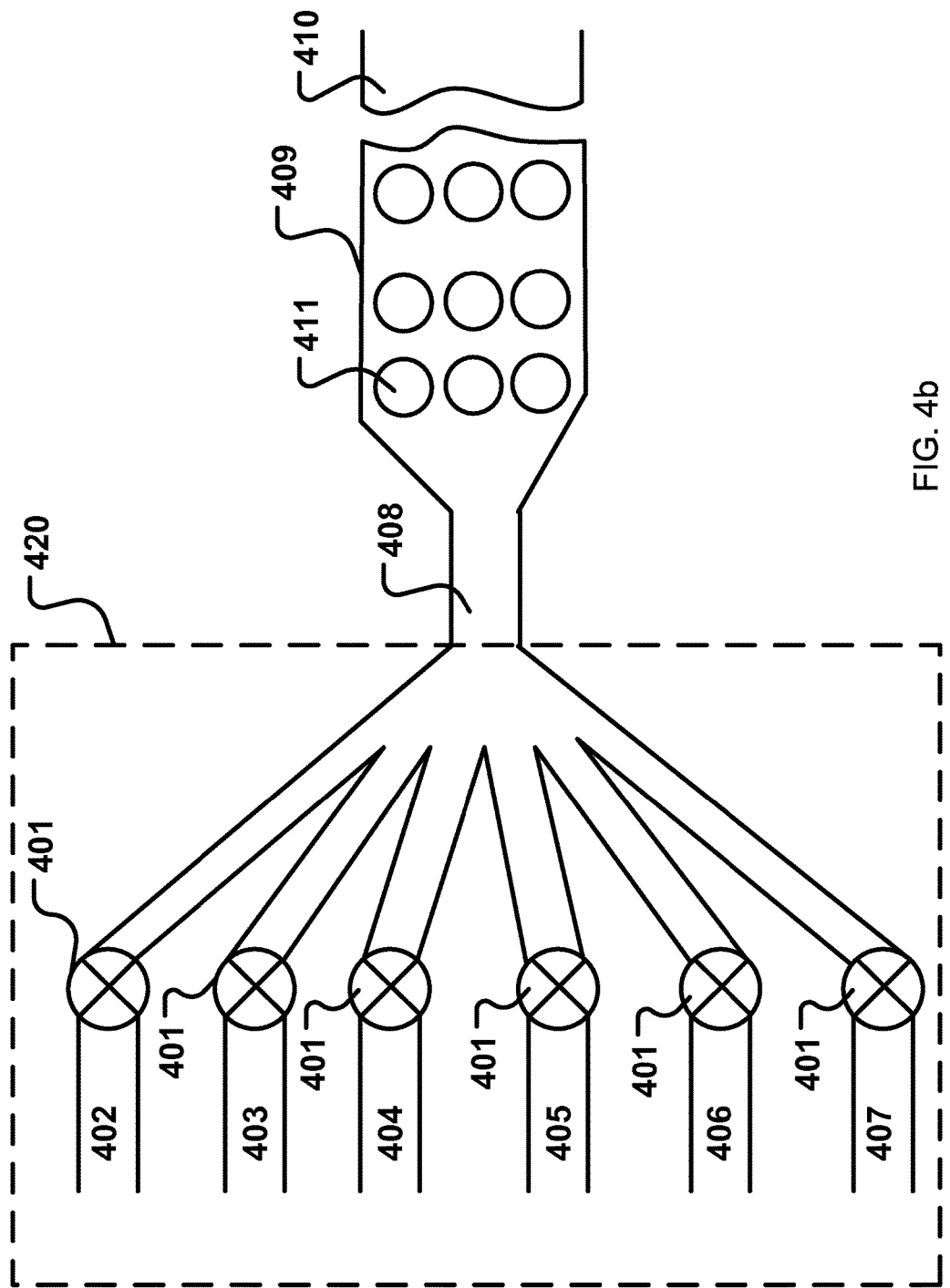
FIG. 4b illustrates another example of a synthesis system.

FIG. 4b shows another example of a monitoring system with a fluid flow control module 420 and a sensor array 409 based on label-free sensors. Each of the fluid input units 402, 403, 404, 405, 406 and 407 is connected to a respective switch 401. To selectively input a fluid type through one of the fluid input units 402, 403, 404, 405, 406 and 407, the respective switch is used. Remaining components of the monitoring system are similar to the system shown in FIG. 4a.

In the label-free sensors of the sensor array 409, the sensor surface can be functionalized to have a target genetic structure, such as a nucleic acid sequence held within an optical mode, for example by attachment to the sensor surface. Functionalizing the sensor surface can be accomplished by various surface chemistry techniques. A single strand or a small number of strands can be attached to the sensor surface. Once the sensor surface is functionalized with a strand or strands of the target nuclei acid sequence, solid phase synthesis can be performed.

In some implementations, the monitoring system of FIGS. 4a and 4b can be used to functionalize the sensor surface by attaching the species of the target nucleic acid sequence in large numbers. To achieve large numbers of the species, the desired species can be purified and amplified, as needed. The NA can be covalently linked, hybridized to a template, or held by binding to a protein. The NA can further be held directly on the surface, or held in a porous film, such as a gel, hydrogel or sol-gel.

For solid phase synthesis, the monitoring system of FIGS. 4a-b can be used to amplify the target sequence only in the active sensing region of the sensor. To amplify the target sequence only, selectively bound primer and hybridization sequences can be used. This can be achieved using synthesis in situ, photopatterning, or masking techniques for example. Photopatterning of the primer could be achieved using ultraviolet (UV) sensitive binding chemistry. The desired selectivity could be achieved by using a mask layer formed out of a material that does not allow surface binding, such as a Teflon based material. This material itself can be patterned using lithographic approaches and other techniques.

The monitoring systems of FIGS. 4a-b can be used in applications where the target sequence is bound in sufficiently large numbers, and an active surface is provided for binding only in the region of the sensor. This surface treatment can be more generic and may not need to contain primers or specific hybridization sequences. However, for some applications, providing a hybridization sequence for a known portion of a target molecule may be advantageous.

For example, in the case of a single nucleotide polymorphism assay, most of the target sequence is known, and a hybridization probe could be designed to pull down the particular piece of nucleic acid of interest. Then, sequencing can take place on the unknown region to expose additions, deletions, substitutions, and other mutations of interest.

The monitoring system of FIGS. 4a-b can be used to provide a combination of multi-strand attachment and an amplification process for the multi-strand attachment. For example, hybridization of a sample could be obtained using known probe sequences, and then solid phase amplification could be performed to boost the numbers.

In some implementations, the solid phase amplification could be performed in solution, perhaps in real time, while hybridization is occurring on the sensors. For example, the sensors in the synthesis system can be placed in a solution undergoing standard Polymerase Chain Reaction (PCR) that performs amplification.

By using these techniques for target NA attachment to the sensor, the amount of target material can be measured. This allows accurate calibration of the target material amount on the sensors. Such accurate calibration of the target material amount allows normalization of the subsequent synthesis reactions, and allows a user to determine when an appropriate quantity of target sequence has been accumulated to proceed with synthesis. This can be observed in real time by making a rapid succession of measurements during the target NA attachment and/or amplification process. Also, measurements can be made at significant points in the process, such as between PCR cycles. With knowledge of the sensor response prior to attachment and during/after attachment, the amount of target material attached can be determined.

In the monitoring systems of FIGS. 4a-b, any inadvertently or non-selectively bound materials can be removed from the sensor surface. The removal can be achieved by any of a number of well known techniques, such as washing and modification of the astringency of the sensor, for example but not limited to heating and/or changing the salt concentration or pH of the ambient solution.

Real time examination of the sensors can provide information regarding the progress of the removal process. In addition, feedback information can be provided to determine when to stop washing, or when to stop heating the target material. For example, the ambient solution can be heated until the non-selectively bound material has been melted off the sensors. However, the temperature is kept below a point where the target sequence would be completely removed. By watching the rate at which the non-desired material is removed, an assessment of which temperature to use, and when to stop heating could be accomplished. A similar approach could be used to regulate the number of wash cycles.

The monitoring systems of FIGS. 4a-b can be used in applications where a large number of different target species are present in the same analyte. The system can be used to control the surface attachment conditions to deposit only one species on each sensor. For example, the sensor array 409 can be designed to include multiple sensors with each sensor masked in such a manner to provide surface attachment on the sensor. The concentration, reaction time, temperature, etc., can be modified to statistically allow only a single target molecule to deposit within each sensor region. Subsequent solid phase amplification can increase the number of target molecules up to an appropriate level for observation of synthesis.

The potential issues with this single species attachment approach include the possibilities that more than one species is deposited on a single sensor, or no deposition occurs on a particular sensor. Both of the non-single species cases can be screened for during synthesis. For example, when more than one species attach to a single sensor, an irregular sensor response is obtained because only a fractional proportion of sites is available for the addition of a particular base. This reduction of available sites can result in a fractional sensor response in comparison to a uniformly hybridized sensor. Sensors with no target molecules provides little to no response. In such manners, a good sensor (single species attachment) can be distinguished from a bad sensor (multiple of no species attachment) during the course of the synthesis process.

After target molecule attachment, the remainder of active surface binding sites can be removed or blocked to prevent the accumulation of non-selectively bound material. Because the non-selectively bound material can inhibit the accuracy of measurement, blocking the remaining active surface binding sites can provide a more accurate result.

The monitoring systems of FIGS. 4a-b can be used to perform NA synthesis using a number of techniques. For example, a polymerase and its associated buffer solutions can be used to perform the synthesis. When the sensors of the synthesis system include an evanescent field sensor, the polymerase and buffer solutions can cause a measurable offset to the sensor response. This offset can be addressed in a number of ways. The synthesis can be performed in conditions that encourage a steady state polymerase attachment condition. The steady state polymerase attachment results in a steady offset, and the desired synthesis signal is the delta off of this baseline offset. The baseline offset may change as the synthesis processes.

Also, the polymerase can be driven off of the target sequence to perform the read, and then reattached when proceeding to subsequent base addition. When the polymerase is detached, the polymerase can remain in the ambient solution or washed away from the sensor region and then subsequently replaced. For a single synthesis step, such as that needed in a single nucleotide polymorphism (SNP) reaction, removing the polymerase is not critical because subsequent reattachment is not necessarily required. When large numbers of bases are to be synthesized, then it is advantageous to keep the polymerase attached, if possible.

The monitoring systems of FIGS. 4a-b can be used to detect a genetic variation called Single Nucleotide Polymorphisms (SNPs). SNPs are commonly determined through use of hybridization arrays containing each of the 4 possible variants as part of a 25-mer strand of DNA. To detect SNPs, appropriately prepared DNA is exposed to the hybridization arrays. An array element with the strongest binding indicates the SNP type present. In the monitoring systems of FIGS. 4a-b, a hybridization array is prepared on a label-free sensor, where the hybridization sequence is designed to bind to the DNA proximal to the SNP location, but leaving the SNP base exposed for sequencing by synthesis. The hybridization array can be designed on the label-free sensor such that the SNP is the next base in sequence. Also, the hybridization array can be designed on the label-free sensor such that the SNP is a known number of bases from the termination of the hybridization sequence. In either case, sequencing by synthesis is performed as described above, and the identity of the SNP can be determined based on sensor response.

The monitoring systems of FIGS. 4a-b can be implemented to allow different bases to flow sequentially over the sensors. The monitoring systems of FIGS. 4a-b can be designed to pump different bases in sequence over the sensors. The flow can be continuous, or it can be stopped once the desired mixture is over the sensor region. Between the different solutions containing the different bases, a number of other functional solutions can be added.

FIGS. 5a-d illustrate examples of a sequence of different solutions which can be applied over the sensors in a sensor array. FIG. 5a shows a basic configuration of a synthesis mixture that allows addition of dNTPs or NA bases in sequential order. In this example, the dATP or base A is applied over the sensors (e.g., sensors in the sensor array 409 of the monitoring systems) and a measurement is made. After the bases or dATP, dCTP, dTTP, dGTP, etc. are sequentially applied over the sensors. The synthesis enzyme (such as polymerase) may be optionally added with each dNTP or base. The synthesis enzyme can be added prior to the dNTP or base if the synthesis enzyme maintains a steady or otherwise predictable behavior. Also, the synthesis enzyme can be included with all solutions to guarantee the presence of the enzyme.

The sequence of solution in FIG. 5b shows a buffer solution, B, applied between the different dNTPs or bases. For example, the sensors can be washed between dNTPs or bases. A washing solution, such as a buffer, B, can be added to the sequence of reagents applied over the sensors, potentially between each successive dNTP or base nucleotide solution. The buffer solution, B, is applied to ensure that the previous dNTP or base has been swept or washed from the reaction region prior to addition of the next dNTP or base. For example, the buffer solution is applied between application of dATP or base A and buffer B to prevent or reduce comingling of dATP and B (or bases A and B). This ensures that each base addition is separated by time and solution and thus can be isolated. The buffer solution can also be used to remove non-selective binding.

In addition, non-mixing regions can be added in the synthesis system to prevent different base solutions from intermixing. This could be accomplished by applying a bubble of air or other non-mixing fluid injected in series with the reagents. Also, a sufficiently large amount of the new type of dNTP or base solution can be applied to guarantee removal of the previous dNTP or base solution.

Even small amounts of the previous base solution remaining in the sensor can become an issue, despite the fact that the previous synthesis step should have been fully reacted. If the new dNTP or base reacts, it is possible that the next subsequent dNTP or base will be next in line to react, and thus, a small number of strands will have skipped ahead one base. This anomaly can be minimized by thorough removal of the old base solution (e.g., by using the washing solution) prior to introduction of the next one.

The sequence of solutions in FIG. 5c shows adding and removing a synthesis enzyme prior to each base inquiry. For example, a synthesis enzyme, such as polymerase, P, can be added prior to each dNTP or base. The added polymerase, P, is removed before the next dNTP or base is added using a solution that encourages the disassociation of the polymerase with the target strand, RP. Also, after removing the polymerase, another polymerase is added before the next dNTP or base. For example, FIG. 5c shows the addition of polymerase, P, before the addition of dATP or base A. Then, after adding the dATP or base A and before adding the next base, dCTP, the added polymerase, P, is removed using RP. Then another polymerase, P, is added before the dCTP or base. This adding and removing of the polymerase is repeated before addition of each dNTP or base.

The sequence of fluids in FIG. 5d shows a polymerase and associated dNTP or base that are added to obtain a synthesis reaction (A+P). The added polymerase is removed using a solution that disassociation of the polymerase with the target strand, RP. Also, a known buffer that facilitates more accurate measurement, M, of the sensor is added. The addition and removal of the polymerase and the addition of the buffer for measurement are repeated before addition of each dNTP or base.

In some implementations, these fluid sequence options of FIGS. 5a-d are combined in ways that employ one or more of these approaches in a variety of different orders and combinations.

Also, a particular dNTP or base can bind a number of times in a row during a particular sequence. For example, the sequence of A, A-A or A-A-A can react. Such repeated incorporation by a single dNTP or base can be determined by measuring the amplitude of the sensor response. If the complete incorporation of a single base results in a certain response, the complete incorporation of two bases will approximately double the response and three bases will approximately triple the response, etc. Thus by knowing the magnitude of the response quantitatively, multiple additions of a single base type can be determined.

Also, bases that terminate the reaction after the addition of a single nucleotide can be used. However, the use of terminating bases needs additional chemistry to process a series of bases in order to allow the reaction to proceed.

In addition, the monitoring systems of FIGS. 4a-b can be used to evaluate when the addition of a dNTP or base has run to completion. Because it is advantageous to speed up the synthesis reaction rate, real time monitoring of the reaction can be performed. When it is determined that the reaction is complete, or that no reaction is going to occur, the process of introducing the next dNTP or base can be started.

As more and more bases are added to the synthesis product, the location for the additional base may be moving either closer or further from the sensor surface, depending on what primer configuration is employed and how the target sequence is attached to the sensors. For an evanescent field sensor of the monitoring systems shown in FIGS. 4a-b, a non-uniform response can be obtained as a function of proximity to the sensor surface. Thus, the sensor signal can be corrected for this change. The expected signal baseline response can be adjusted as a function of time because the response of the signal has been calibrated for the known location of polymerization reaction or because the signal response is being fit to the known field decay.

This approach is applicable for DNA, RNA or any type of nucleic acid complex which can by sequentially synthesized. In the case of RNA, a conversion to cDNA might be needed prior to any amplification process, but is not absolutely necessary.

This approach can be scaled to high degrees of parallelism by incorporating a large number of sensors and/or scanning systems. For example, many sensors can be employed on a single chip of a synthesis system. Also, many chips can be implemented in a synthesis system to achieve scaling.

In some implementations, the monitoring systems of FIGS. 4a-b can be implemented to include a microfluidic switching manifold in immediate proximity to the sensor(s) to allow more rapid fluidic switching times. Such a microfluidic switching manifold can accelerate the sequencing process.

In some implementations, monitoring systems of FIGS. 4a-b can be used to monitor an enzymatic process, other than synthesis described above, within an optical field of an optical resonator. An enzymatic process can result in a modification of the nucleic acid when one or more enzymes are applied. Examples of the enzymatic process can include one or the following reactions: (1) polymerase driven base extension; (2) polymerase repair activity driven base excision; (3) reverse transcriptase driven DNA extension; (4) reverse transcriptase driven RNA exonuclease activity; (5) DNA cleavage driven by site specific endonuclease activity; (6) annealing driven by ligase enzyme activity and or topoisomerase action and or recombination enzymes; (7) phosphorylation driven by kinase; (8) dephosphorylation driven by phosphatase; (9) RNA Splicing driven by splicing enzymes and or catalytic RNA splicing fragments; and (10) cleavage through miRNA driven DICER complex.

Figure 6:
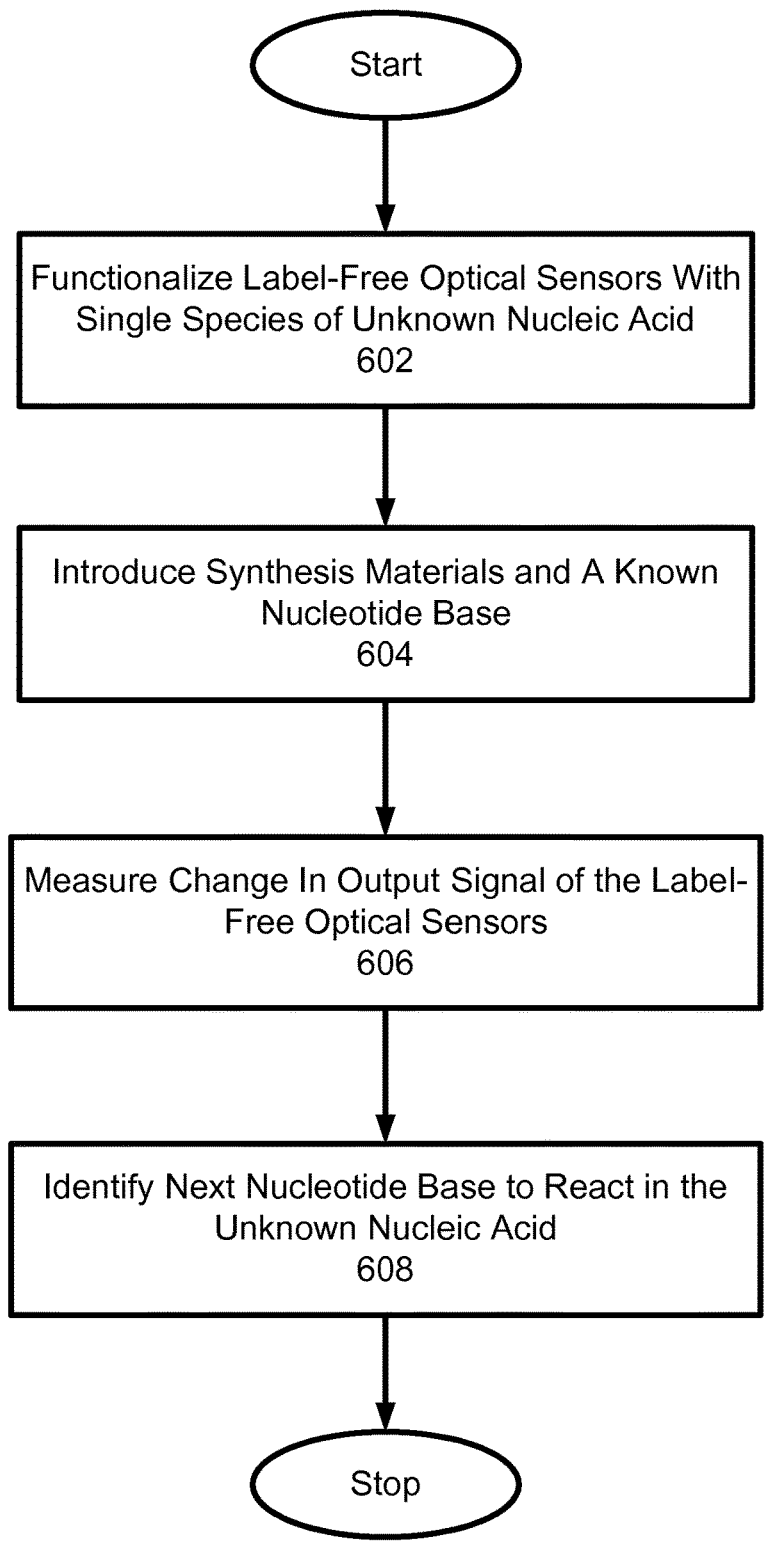
FIG. 6 shows an example process for synthesizing a nucleic acid.

FIG. 6 shows an example process for synthesizing a nucleic acid. Label-free optical sensors are functionalized with a single species of an unknown nucleic acid (602). A reagent comprising synthesis materials and a known dNTP or base is selectively introduced to the unknown species of nucleic acid (604). A change in an output signal of the label-free optical sensor is measured to detect synthesis of the nucleic acid when a nucleotide base in the unknown species of nucleic acid matches with the known dNTP base (606). A next nucleotide base in the unknown nucleic acid to react is identified based on the introduced known dNTP or base and the measured change in the output signal (608). This process can be repeated by applying a sequence of dNTPs or base as shown in FIGS. 5a-d.

Also, a magnitude of the output signal can be measured to determine a number of the introduced known dNTP or base incorporated during the detected synthesis. The unknown species of nucleic acid can be amplified using a selectively bound primer and hybridization sequences. Solid phase amplification and hybridization of the unknown species of nucleic acid can be performed in parallel. An amount of the unknown species of nucleic acid can be measured based on the output signal of the optical sensor before and after functionalization. Not just one but a sequence of known dNTPs or bases can be applied and inadvertently or non-selectively bound dNTPs or bases can be removed by applying a washing agent between the dNTPs or bases. The surface of the optical sensor can be functionalized with a single species of nucleic acid based on the output signal of the optical sensor. Further, measuring a change in an output signal of the label-free optical sensor can include: measuring an output signal of the label-free optical sensor before introducing the known dNTP or base; measuring another output signal of the label-free optical sensor after introducing the known dNTP or base; and identifying a difference between the measured output signals. The unknown species of nucleic acid can be held within an evanescent field.

Figure 7:
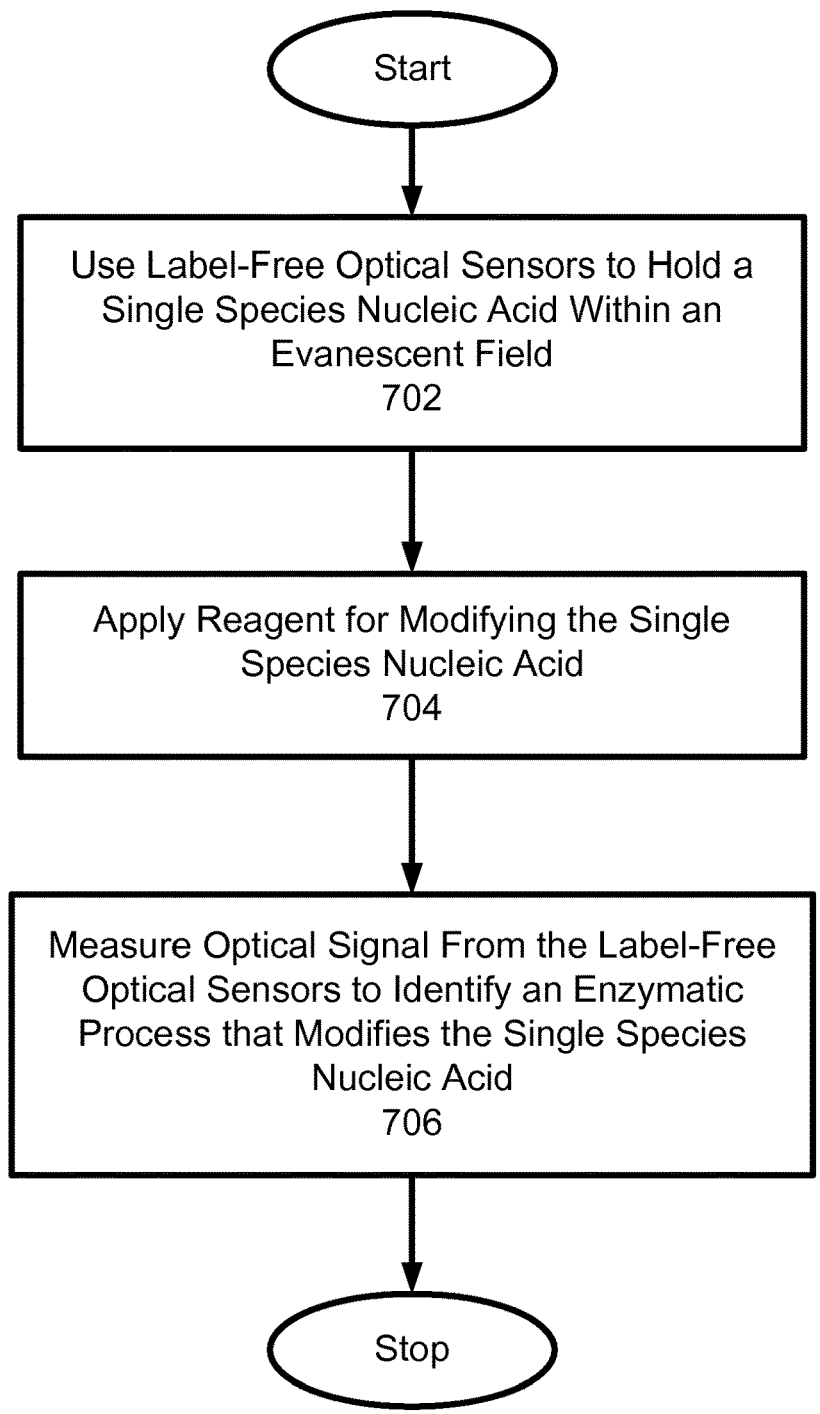
FIG. 7 shows an example process for monitoring an enzymatic process within an optical field of a label-free optical resonator.

FIG. 7 shows an example process for monitoring an enzymatic process within an optical field of a label-free optical resonator. Label-free optical sensors can be used to hold a single species nucleic acid within an evanescent field (702). A reagent for modifying the single species nucleic acid is applied to the single species of nucleic acid (704). An optical signal from the label-free optical resonator is measured in response to the applied reagent to identify an enzymatic process that results in a modification of the nucleic acid (706). The enzymatic process can include one of the following reactions: polymerase driven base extension; polymerase repair activity driven base excision; reverse transcriptase driven DNA extension; reverse transcriptase driven RNA exonuclease activity; DNA cleavage driven by site specific endonuclease activity; annealing driven by ligase enzyme activity and or topoisomerase action and or recombination enzymes; phosphorylation driven by kinase; dephosphorylation driven by phosphatase; RNA Splicing driven by splicing enzymes and or catalytic RNA splicing fragments; and cleavage through miRNA driven DICER complex.

In some implementations, one or more evanescent wave sensors includes multiple nucleic acid bound to the surface of the sensors. The sensors can include a means for introducing a reagent containing all necessary components for synthesis and a base of choice. The sensors can include a means for interrogating the sensors and evaluating if matter is bound.

A method for sequencing can include binding multiple known species of nucleic acid within the range of an evanescent field sensor. A reagent containing synthesis materials and a known base are introduced to the bound species. The change in output from the evanescent field sensor is observed to determine if synthesis has occurred. The next base in sequence is determined based on knowledge of which base was present at the time the sensor signal indicates the presence of additional bound material. The sensor can be a resonant cavity. The resonant cavity can be a ring resonator. The ring resonator can be made primarily of silicon and the ring is disposed on a silicon-on-insulator wafer.

One or more evanescent wave sensors can include a plurality of a substantially single species nucleic acid held within the evanescent field, a means for controllably introducing a reagent and components for modification of the nucleic acid, and a label-free means for interrogating the sensor and evaluating if the nucleic acid is modified. One or more evanescent wave sensors can include a plurality of a substantially single species nucleic acid bound to the surface, a means for introducing a reagent containing all necessary components for synthesis, and a base of choice, and a label-free means for interrogating the sensor and evaluating if matter is bound.

A method for sequencing nucleic acids can include holding a plurality of an unknown species of nucleic acid within the range of an evanescent field sensor, introducing a reagent containing synthesis materials and a known base to the bound species, observing the change in output from the evanescent field sensor to determine if synthesis has occurred, and determining the next base in sequence based on knowledge of which base was present at the time the sensor signal indicates the present of additional bound matter.

An optical resonator can be used to monitor an enzymatic process occurring within the optical field of said resonator. The enzymatic process can result in a modification of the nucleic acid, such as: polymerase driven base extension, polymerase repair activity driven base excision, reverse transcriptase driven DNA extension, reverse transcriptase driven RNA exonuclease activity, DNA cleavage driven by site specific endonuclease activity, annealing driven by ligase enzyme activity and or topoisomerase action and or recombination enzymes, phosphorylation, driven by kinase, dephosphorylation driven by phosphatase, RNA Splicing driven by splicing enzymes and/or catalytic RNA splicing fragments, or cleavage through miRNA driven DICER complex.

While this specification contains many specifics, these should not be construed as limitations on the scope of an invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or a variation of a subcombination.

Only a few implementations are disclosed. Variations and enhancements of the described implementations and other implementations may be made based what is described and illustrated.

What is claimed is:

1. A system for determining the nucleotide sequence of a target nucleic acid molecule, comprising:
   a substrate;
   a lower cladding layer provided over, and being supported by, said substrate;
   one or more coupling waveguides disposed over said lower cladding layer to input an optical signal;
   an array of label-free optical sensors provided over said lower cladding layer, each of said label-free optical sensors including a waveguide formed into a ring to serve as a ring resonant cavity, each of said ring resonant cavities in proximity to at least one of said one or more coupling waveguides with a spacing that provides an evanescent coupling region between said coupling waveguide and said ring resonant cavity, each label-free optical sensor being configured to modulate an optical signal in response to a nucleotide extension reaction, wherein each label-free optical sensor includes a sensing region that overlaps said evanescent coupling region and is functionalized with a target nucleic acid molecule, and wherein at least a portion of the nucleotide sequence of the target nucleic acid molecule is unknown, and wherein said label-free optical sensors of the array are each configured to produce an optical evanescent field in the sensing region such that when a single nucleotide is added to the target nucleic acid molecule via the nucleotide extension reaction, the label-free optical sensor modulates the optical signal to thereby provide a detectable indication of addition of the single nucleotide to the target nucleic acid molecule;
   a fluid flow control module comprising fluid receiving units to provide paths for different fluids to flow into the fluid flow control module;

at least one switch connected to the fluid receiving units to select a fluid for flowing through the fluid receiving units, wherein the fluid comprises at least a nucleotide base; and a fluid channel connected between the fluid flow control module and the array of label-free optical sensors to allow the selected fluid to flow from the fluid flow control module to the array of label-free optical sensors.

2. The system of claim 1, wherein the resonant cavity has a resonant frequency that shifts in response to the nucleotide extension reaction.

3. The system of claim 1, wherein the array of label-free optical sensors is configured to be interrogated.

4. The system of claim 1, wherein the resonant cavity has a complex refractive index of the resonant cavity that changes in response to the nucleotide extension reaction.

5. The system of claim 1, further comprising the fluid with a nucleotide base, the fluid having a single type of nucleotide base selected from the group consisting of A, G, C, T, and U.

6. The system of claim 1, further comprising a fluid which comprises a polymerase.

7. The system of claim 1, wherein the array of label-free optical sensors is configured to be interrogated while undergoing the nucleotide extension reaction.

8. The system of claim 1, wherein said substrate comprises a silicon-on-insulator wafer.

9. The system of claim 1, wherein the lower cladding layer comprises a buried insulator layer made of silicon dioxide.

10. The system of claim 1, wherein the at least one coupling waveguide comprises two coupling waveguides in evanescent coupling with said waveguide comprising said ring resonator cavity.

11. A system for determining the nucleotide sequence of a target nucleic acid molecule, comprising:
a substrate;
a lower cladding layer provided over, and being supported by, said substrate;
one or more coupling waveguides disposed over said lower cladding layer to input an optical signal;
a sensor array provided over said lower cladding layer, the sensor array comprising a plurality of optical resonators, each of said plurality of optical resonators being a waveguide formed in a closed waveguide loop, each of said optical resonators in proximity to at least one of said one or more coupling waveguides with a spacing that provides an evanescent coupling region between said coupling waveguide and said optical resonator;
an upper cladding layer provided over said plurality of optical resonators and said one or more coupling waveguides, said upper cladding layer including one or more cavities each at least partially surrounding a respective evanescent coupling region to serve as a sensing region, wherein each sensing region is functionalized with at least one target nucleic acid molecule, and wherein at least a portion of the nucleotide sequence of the target nucleic acid molecule is unknown, and wherein each resonator is configured such that, when a single nucleotide is added to the target nucleic acid molecule via a nucleotide extension reaction, the resonator detectably modulates the optical signal to thereby provide a detectable indication of addition of the single nucleotide to the target nucleic acid molecule;
a fluid flow control module; and
a flow channel in fluid communication with the sensor array, wherein the flow channel is configured to allow fluid to flow from the fluid flow control module to the sensor array.

12. The system of claim 11, wherein each resonant cavity has a resonant frequency that shifts in response to the nucleotide extension reaction.

13. The system of claim 11, wherein the sensor array is configured to be interrogated.

14. The system of claim 11, wherein each resonant cavity has a complex refractive index that changes in response to the nucleotide extension reaction.

15. The system of claim 11, wherein said closed waveguide loop comprises a closed waveguide loop of circular shape.

16. The system of claim 11, wherein said closed waveguide loop comprises a closed waveguide loop of non-circular shape.

17. The system of claim 11, wherein said closed waveguide loop has an irregular shape.

18. The system of claim 11, wherein said closed waveguide loop has an elliptical shape.

* * * * *